(12) United States Patent
Houser

(10) Patent No.: US 9,050,124 B2
(45) Date of Patent: Jun. 9, 2015

(54) ULTRASONIC SURGICAL INSTRUMENT AND CARTILAGE AND BONE SHAPING BLADES THEREFOR

(75) Inventor: Kevin L. Houser, Springboro, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 13/545,292

(22) Filed: Jul. 10, 2012

(65) Prior Publication Data
US 2013/0012970 A1 Jan. 10, 2013

Related U.S. Application Data

(62) Division of application No. 12/732,702, filed on Mar. 26, 2010, now Pat. No. 8,236,019, which is a division of application No. 11/726,621, filed on Mar. 22, 2007, now abandoned.

(51) Int. Cl.
| | |
|---|---|
| A61B 17/32 | (2006.01) |
| A61B 17/16 | (2006.01) |
| A61B 17/22 | (2006.01) |

(52) U.S. Cl.
CPC . *A61B 17/320068* (2013.01); *A61B 2017/1602* (2013.01); *A61B 2017/22079* (2013.01); *A61B 2017/320008* (2013.01); *A61B 2017/320072* (2013.01); *A61B 2017/320076* (2013.01); *A61B 2017/32008* (2013.01); *A61B 2017/320084* (2013.01); *A61B 2217/005* (2013.01)

(58) Field of Classification Search
CPC .............. A61B 17/320068; A61B 2017/1602; A61B 2017/22079; A61B 2017/320008; A61B 2017/320072

USPC ............................ 600/564, 565, 568; 604/22; 606/167–171
See application file for complete search history.

(56) References Cited

U.S. PATENT DOCUMENTS

| | | | |
|---|---|---|---|
| 969,528 | A | 9/1910 | Disbrow |
| 1,570,025 | A | 1/1926 | Young |
| 2,704,333 | A | 3/1955 | Calosi et al. |
| 2,736,960 | A | 3/1956 | Armstrong |
| 2,849,788 | A | 9/1958 | Creek |
| RE25,033 | E | 8/1961 | Balamuth et al. |
| 3,015,961 | A | 1/1962 | Roney |

(Continued)

FOREIGN PATENT DOCUMENTS

| | | |
|---|---|---|
| CN | 1634601 A | 7/2005 |
| CN | 1640365 A | 7/2005 |

(Continued)

OTHER PUBLICATIONS

"Round", www.merriam-webster.com/dictionary/round, Oct. 25, 2013, p. 1.*

(Continued)

*Primary Examiner* — Ashley Fishback

(57) ABSTRACT

An ultrasonic surgical blade that includes a blade body that has a treatment region. At least one indentation can be formed in the treatment region of the blade body wherein each indentation forms a tissue cutting edge with an outer surface of the blade body. The indentation may comprise one or more holes, lumens, grooves or dimples or a combination of such structures. In various embodiments, one or more aspiration lumens are provided in the surgical blade which may ultimately communicate with an aspiration lumen or passage in an ultrasonic surgical instrument.

12 Claims, 10 Drawing Sheets

(56) References Cited

U.S. PATENT DOCUMENTS

| | | |
|---|---|---|
| 3,513,848 A | 5/1970 | Winston et al. |
| 3,526,219 A | 9/1970 | Balamuth |
| 3,614,484 A | 10/1971 | Shoh |
| 3,636,943 A | 1/1972 | Balamuth |
| 3,776,238 A | 12/1973 | Peyman et al. |
| 3,805,787 A | 4/1974 | Banko |
| 3,830,098 A | 8/1974 | Antonevich |
| 3,854,737 A | 12/1974 | Gilliam, Sr. |
| 3,862,630 A | 1/1975 | Balamuth |
| 3,900,823 A | 8/1975 | Sokal et al. |
| 3,918,442 A | 11/1975 | Nikolaev et al. |
| 3,946,738 A | 3/1976 | Newton et al. |
| 3,955,859 A | 5/1976 | Stella et al. |
| 3,956,826 A | 5/1976 | Perdreaux, Jr. |
| 4,156,187 A | 5/1979 | Murry et al. |
| 4,188,927 A | 2/1980 | Harris |
| 4,200,106 A | 4/1980 | Douvas et al. |
| 4,306,570 A | 12/1981 | Matthews |
| 4,445,063 A | 4/1984 | Smith |
| 4,491,132 A | 1/1985 | Aikins |
| 4,504,264 A | 3/1985 | Kelman |
| 4,574,615 A | 3/1986 | Bower et al. |
| 4,617,927 A | 10/1986 | Manes |
| 4,633,119 A | 12/1986 | Thompson |
| 4,634,420 A | 1/1987 | Spinosa et al. |
| 4,640,279 A | 2/1987 | Beard |
| 4,649,919 A | 3/1987 | Thimsen et al. |
| 4,708,127 A | 11/1987 | Abdelghani |
| 4,712,722 A | 12/1987 | Hood et al. |
| 4,827,911 A | 5/1989 | Broadwin et al. |
| 4,832,683 A | 5/1989 | Idemoto et al. |
| 4,838,853 A | 6/1989 | Parisi |
| 4,850,354 A | 7/1989 | McGurk-Burleson et al. |
| 4,865,159 A | 9/1989 | Jamison |
| 4,896,009 A | 1/1990 | Pawlowski |
| 4,903,696 A | 2/1990 | Stasz et al. |
| 4,922,902 A | 5/1990 | Wuchinich et al. |
| 4,965,532 A | 10/1990 | Sakurai |
| 4,979,952 A | 12/1990 | Kubota et al. |
| 4,981,756 A | 1/1991 | Rhandhawa |
| 5,026,387 A | 6/1991 | Thomas |
| 5,109,819 A | 5/1992 | Custer et al. |
| 5,112,300 A | 5/1992 | Ureche |
| 5,123,903 A | 6/1992 | Quaid et al. |
| 5,126,618 A | 6/1992 | Takahashi et al. |
| 5,162,044 A | 11/1992 | Gahn et al. |
| 5,163,537 A | 11/1992 | Radev |
| 5,167,725 A | 12/1992 | Clark et al. |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| 5,213,569 A | 5/1993 | Davis |
| 5,221,282 A | 6/1993 | Wuchinich |
| 5,226,909 A | 7/1993 | Evans et al. |
| 5,226,910 A | 7/1993 | Kajiyama et al. |
| 5,241,236 A | 8/1993 | Sasaki et al. |
| 5,257,988 A | 11/1993 | L'Esperance, Jr. |
| 5,261,922 A | 11/1993 | Hood |
| 5,263,957 A | 11/1993 | Davison |
| 5,275,609 A | 1/1994 | Pingleton et al. |
| 5,282,800 A | 2/1994 | Foshee et al. |
| 5,304,115 A | 4/1994 | Pflueger et al. |
| D347,474 S | 5/1994 | Olson |
| 5,322,055 A | 6/1994 | Davison et al. |
| 5,324,299 A | 6/1994 | Davison et al. |
| 5,326,342 A | 7/1994 | Pflueger et al. |
| 5,344,420 A | 9/1994 | Hilal et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,366,466 A | 11/1994 | Christian et al. |
| 5,371,429 A | 12/1994 | Manna |
| D354,564 S | 1/1995 | Medema |
| 5,381,067 A | 1/1995 | Greenstein et al. |
| 5,403,312 A | 4/1995 | Yates et al. |
| D358,887 S | 5/1995 | Feinberg |
| 5,411,481 A | 5/1995 | Allen et al. |
| 5,419,761 A | 5/1995 | Narayanan et al. |
| 5,421,829 A | 6/1995 | Olichney et al. |
| 5,438,997 A | 8/1995 | Sieben et al. |
| 5,449,370 A | 9/1995 | Vaitekunas |
| 5,471,988 A | 12/1995 | Fujio et al. |
| 5,483,501 A | 1/1996 | Park et al. |
| 5,486,162 A | 1/1996 | Brumbach |
| 5,500,216 A | 3/1996 | Julian et al. |
| 5,501,654 A | 3/1996 | Failla et al. |
| 5,505,693 A | 4/1996 | Mackool |
| 5,507,738 A | 4/1996 | Ciervo |
| 5,527,331 A | 6/1996 | Kresch et al. |
| 5,562,609 A | 10/1996 | Brumbach |
| 5,562,610 A | 10/1996 | Brumbach |
| 5,577,654 A | 11/1996 | Bishop |
| 5,601,601 A | 2/1997 | Tal et al. |
| 5,603,773 A | 2/1997 | Campbell |
| 5,607,436 A | 3/1997 | Pratt et al. |
| 5,618,492 A | 4/1997 | Auten et al. |
| 5,628,760 A | 5/1997 | Knoepfler |
| 5,630,420 A | 5/1997 | Vaitekunas |
| D381,077 S | 7/1997 | Hunt |
| 5,651,780 A | 7/1997 | Jackson et al. |
| 5,653,713 A | 8/1997 | Michelson |
| 5,669,922 A | 9/1997 | Hood |
| 5,674,235 A | 10/1997 | Parisi |
| 5,690,269 A | 11/1997 | Bolanos et al. |
| 5,694,936 A | 12/1997 | Fujimoto et al. |
| 5,713,896 A | 2/1998 | Nardella |
| 5,730,752 A | 3/1998 | Alden et al. |
| 5,733,074 A | 3/1998 | Stöck et al. |
| 5,741,226 A | 4/1998 | Strukel et al. |
| 5,792,135 A | 8/1998 | Madhani et al. |
| 5,792,165 A | 8/1998 | Klieman et al. |
| 5,808,396 A | 9/1998 | Boukhny |
| 5,810,859 A | 9/1998 | DiMatteo et al. |
| 5,817,084 A | 10/1998 | Jensen |
| 5,817,119 A | 10/1998 | Klieman et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,843,109 A | 12/1998 | Mehta et al. |
| 5,878,193 A | 3/1999 | Wang et al. |
| 5,879,364 A | 3/1999 | Bromfield et al. |
| 5,883,615 A | 3/1999 | Fago et al. |
| 5,893,835 A | 4/1999 | Witt et al. |
| 5,897,523 A | 4/1999 | Wright et al. |
| 5,897,569 A | 4/1999 | Kellogg et al. |
| 5,906,628 A | 5/1999 | Miyawaki et al. |
| 5,911,699 A | 6/1999 | Anis et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| D416,089 S | 11/1999 | Barton et al. |
| 5,980,510 A | 11/1999 | Tsonton et al. |
| 5,989,274 A | 11/1999 | Davison et al. |
| 5,989,275 A | 11/1999 | Estabrook et al. |
| 5,993,972 A | 11/1999 | Reich et al. |
| 6,024,741 A | 2/2000 | Williamson, IV et al. |
| 6,027,515 A | 2/2000 | Cimino |
| 6,033,375 A | 3/2000 | Brumbach |
| 6,050,943 A | 4/2000 | Slayton et al. |
| 6,051,010 A | 4/2000 | DiMatteo et al. |
| 6,056,735 A | 5/2000 | Okada et al. |
| 6,063,098 A | 5/2000 | Houser et al. |

(56) References Cited

U.S. PATENT DOCUMENTS

| | | |
|---|---|---|
| 6,066,132 A | 5/2000 | Chen et al. |
| 6,066,151 A | 5/2000 | Miyawaki et al. |
| 6,068,647 A | 5/2000 | Witt et al. |
| 6,077,285 A | 6/2000 | Boukhny |
| 6,083,191 A | 7/2000 | Rose |
| 6,086,584 A | 7/2000 | Miller |
| 6,090,120 A | 7/2000 | Wright et al. |
| 6,109,500 A | 8/2000 | Alli et al. |
| 6,110,127 A | 8/2000 | Suzuki |
| 6,113,594 A | 9/2000 | Savage |
| 6,117,152 A | 9/2000 | Huitema |
| 6,126,629 A | 10/2000 | Perkins |
| 6,129,735 A | 10/2000 | Okada et al. |
| 6,132,368 A | 10/2000 | Cooper |
| 6,139,320 A | 10/2000 | Hahn |
| 6,139,561 A | 10/2000 | Shibata et al. |
| 6,142,615 A | 11/2000 | Qiu et al. |
| 6,147,560 A | 11/2000 | Erhage et al. |
| 6,152,902 A | 11/2000 | Christian et al. |
| 6,159,160 A | 12/2000 | Hsei et al. |
| 6,159,175 A | 12/2000 | Strukel et al. |
| 6,165,150 A | 12/2000 | Banko |
| 6,204,592 B1 | 3/2001 | Hur |
| 6,206,844 B1 | 3/2001 | Reichel et al. |
| 6,210,403 B1 | 4/2001 | Klicek |
| 6,214,023 B1 | 4/2001 | Whipple et al. |
| 6,231,565 B1 | 5/2001 | Tovey et al. |
| 6,233,476 B1 | 5/2001 | Strommer et al. |
| 6,238,366 B1 | 5/2001 | Savage et al. |
| 6,252,110 B1 | 6/2001 | Uemura et al. |
| D444,365 S | 7/2001 | Bass et al. |
| 6,254,623 B1 | 7/2001 | Haibel, Jr. et al. |
| 6,258,034 B1 | 7/2001 | Hanafy |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,278,218 B1 | 8/2001 | Madan et al. |
| 6,283,981 B1 | 9/2001 | Beaupre |
| 6,309,400 B2 | 10/2001 | Beaupre |
| 6,319,221 B1 | 11/2001 | Savage et al. |
| 6,325,811 B1 | 12/2001 | Messerly |
| 6,328,751 B1 | 12/2001 | Beaupre |
| 6,340,352 B1 | 1/2002 | Okada et al. |
| 6,352,532 B1 | 3/2002 | Kramer et al. |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,387,109 B1 | 5/2002 | Davison et al. |
| 6,388,657 B1 | 5/2002 | Natoli |
| 6,391,042 B1 | 5/2002 | Cimino |
| 6,405,733 B1 | 6/2002 | Fogarty et al. |
| 6,416,486 B1 | 7/2002 | Wampler |
| 6,423,073 B2 | 7/2002 | Bowman |
| 6,423,082 B1 | 7/2002 | Houser et al. |
| 6,428,539 B1 | 8/2002 | Baxter et al. |
| 6,432,118 B1 | 8/2002 | Messerly |
| 6,436,114 B1 | 8/2002 | Novak et al. |
| 6,436,115 B1 | 8/2002 | Beaupre |
| 6,443,969 B1 | 9/2002 | Novak et al. |
| 6,454,781 B1 | 9/2002 | Witt et al. |
| 6,454,782 B1 | 9/2002 | Schwemberger |
| 6,458,142 B1 | 10/2002 | Faller et al. |
| 6,480,796 B2 | 11/2002 | Wiener |
| 6,485,490 B2 | 11/2002 | Wampler et al. |
| 6,491,708 B2 | 12/2002 | Madan et al. |
| 6,497,715 B2 | 12/2002 | Satou |
| 6,500,176 B1 | 12/2002 | Truckai et al. |
| 6,500,188 B2 | 12/2002 | Harper et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,533,784 B2 | 3/2003 | Truckai et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,561,983 B2 | 5/2003 | Cronin et al. |
| 6,572,632 B2 | 6/2003 | Zisterer et al. |
| 6,575,969 B1 | 6/2003 | Rittman, III et al. |
| 6,582,451 B1 | 6/2003 | Marucci et al. |
| 6,589,200 B1 | 7/2003 | Schwemberger et al. |
| 6,589,239 B2 | 7/2003 | Khandkar et al. |
| 6,610,059 B1 | 8/2003 | West, Jr. |
| 6,616,450 B2 | 9/2003 | Mossle et al. |
| 6,623,501 B2 | 9/2003 | Heller et al. |
| 6,626,926 B2 | 9/2003 | Friedman et al. |
| 6,633,234 B2 | 10/2003 | Wiener et al. |
| 6,656,177 B2 | 12/2003 | Truckai et al. |
| 6,662,127 B2 | 12/2003 | Wiener et al. |
| 6,663,941 B2 | 12/2003 | Brown et al. |
| 6,669,690 B1 | 12/2003 | Okada et al. |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,899 B2 | 1/2004 | Wiener et al. |
| 6,682,544 B2 | 1/2004 | Mastri et al. |
| 6,689,146 B1 | 2/2004 | Himes |
| 6,716,215 B1 | 4/2004 | David et al. |
| 6,731,047 B2 | 5/2004 | Kauf et al. |
| 6,733,506 B1 | 5/2004 | McDevitt et al. |
| 6,762,535 B2 | 7/2004 | Take et al. |
| 6,770,072 B1 | 8/2004 | Truckai et al. |
| 6,773,443 B2 | 8/2004 | Truwit et al. |
| 6,773,444 B2 | 8/2004 | Messerly |
| 6,783,524 B2 | 8/2004 | Anderson et al. |
| 6,786,382 B1 | 9/2004 | Hoffman |
| 6,786,383 B2 | 9/2004 | Stegelmann |
| 6,790,216 B1 | 9/2004 | Ishikawa |
| D496,997 S | 10/2004 | Dycus et al. |
| 6,802,843 B2 | 10/2004 | Truckai et al. |
| 6,827,712 B2 | 12/2004 | Tovey et al. |
| 6,828,712 B2 | 12/2004 | Battaglin et al. |
| 6,869,439 B2 | 3/2005 | White et al. |
| 6,875,220 B2 | 4/2005 | Du et al. |
| 6,905,497 B2 | 6/2005 | Truckai et al. |
| 6,908,472 B2 | 6/2005 | Wiener et al. |
| 6,913,579 B2 | 7/2005 | Truckai et al. |
| 6,923,804 B2 | 8/2005 | Eggers et al. |
| 6,926,716 B2 | 8/2005 | Baker et al. |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,677 B2 | 9/2005 | Nita et al. |
| 6,945,981 B2 | 9/2005 | Donofrio et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,984,220 B2 | 1/2006 | Wuchinich |
| 7,001,335 B2 | 2/2006 | Adachi et al. |
| 7,011,657 B2 | 3/2006 | Truckai et al. |
| 7,033,357 B2 | 4/2006 | Baxter et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,070,597 B2 | 7/2006 | Truckai et al. |
| 7,074,219 B2 | 7/2006 | Levine et al. |
| 7,077,039 B2 | 7/2006 | Gass et al. |
| 7,077,853 B2 | 7/2006 | Kramer et al. |
| 7,083,619 B2 | 8/2006 | Truckai et al. |
| 7,087,054 B2 | 8/2006 | Truckai et al. |
| 7,090,672 B2 | 8/2006 | Underwood et al. |
| 7,101,371 B2 | 9/2006 | Dycus et al. |
| 7,101,378 B2 | 9/2006 | Salameh et al. |
| 7,108,695 B2 | 9/2006 | Witt et al. |
| 7,112,201 B2 | 9/2006 | Truckai et al. |
| D531,311 S | 10/2006 | Guerra et al. |
| 7,118,564 B2 | 10/2006 | Ritchie et al. |
| 7,124,932 B2 | 10/2006 | Isaacson et al. |

(56) References Cited

U.S. PATENT DOCUMENTS

| | | |
|---|---|---|
| 7,125,409 B2 | 10/2006 | Truckai et al. |
| 7,135,018 B2 | 11/2006 | Ryan et al. |
| 7,135,030 B2 | 11/2006 | Schwemberger et al. |
| 7,144,403 B2 | 12/2006 | Booth |
| 7,153,315 B2 | 12/2006 | Miller |
| D536,093 S | 1/2007 | Nakajima et al. |
| 7,156,189 B1 | 1/2007 | Bar-Cohen et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,299 B2 | 1/2007 | Baily |
| 7,163,548 B2 | 1/2007 | Stulen et al. |
| 7,169,146 B2 | 1/2007 | Truckai et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| D541,418 S | 4/2007 | Schechter et al. |
| 7,204,820 B2 | 4/2007 | Akahoshi |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,229,455 B2 | 6/2007 | Sakurai et al. |
| 7,273,483 B2 | 9/2007 | Wiener et al. |
| 7,285,895 B2 | 10/2007 | Beaupré |
| 7,309,849 B2 | 12/2007 | Truckai et al. |
| 7,311,709 B2 | 12/2007 | Truckai et al. |
| 7,317,955 B2 | 1/2008 | McGreevy |
| 7,326,236 B2 | 2/2008 | Andreas et al. |
| 7,331,410 B2 | 2/2008 | Yong et al. |
| 7,353,068 B2 | 4/2008 | Tanaka et al. |
| 7,354,440 B2 | 4/2008 | Truckai et al. |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,390,317 B2 | 6/2008 | Taylor et al. |
| 7,404,508 B2 | 7/2008 | Smith et al. |
| 7,408,288 B2 | 8/2008 | Hara |
| D576,725 S | 9/2008 | Shumer et al. |
| D578,643 S | 10/2008 | Shumer et al. |
| D578,644 S | 10/2008 | Shumer et al. |
| D578,645 S | 10/2008 | Shumer et al. |
| 7,431,704 B2 | 10/2008 | Babaev |
| 7,441,684 B2 | 10/2008 | Shelton, IV et al. |
| 7,455,208 B2 | 11/2008 | Wales et al. |
| 7,472,815 B2 | 1/2009 | Shelton, IV et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,488,285 B2 | 2/2009 | Honda et al. |
| 7,494,468 B2 | 2/2009 | Rabiner et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,524,320 B2 | 4/2009 | Tierney et al. |
| 7,530,986 B2 | 5/2009 | Beaupre et al. |
| 7,534,243 B1 | 5/2009 | Chin et al. |
| D594,983 S | 6/2009 | Price et al. |
| 7,549,564 B2 | 6/2009 | Boudreaux |
| 7,559,450 B2 | 7/2009 | Wales et al. |
| 7,567,012 B2 | 7/2009 | Namikawa |
| 7,578,820 B2 | 8/2009 | Moore et al. |
| 7,654,431 B2 | 2/2010 | Hueil et al. |
| 7,665,647 B2 | 2/2010 | Shelton, IV et al. |
| 7,670,334 B2 | 3/2010 | Hueil et al. |
| 7,674,263 B2 | 3/2010 | Ryan |
| 7,691,098 B2 | 4/2010 | Wallace et al. |
| 7,713,202 B2 | 5/2010 | Boukhny et al. |
| 7,714,481 B2 | 5/2010 | Sakai |
| D618,797 S | 6/2010 | Price et al. |
| 7,751,115 B2 | 7/2010 | Song |
| D621,503 S | 8/2010 | Otten et al. |
| 7,770,774 B2 | 8/2010 | Mastri et al. |
| 7,770,775 B2 | 8/2010 | Shelton, IV et al. |
| 7,780,054 B2 | 8/2010 | Wales |
| 7,780,659 B2 | 8/2010 | Okada et al. |
| 7,784,662 B2 | 8/2010 | Wales et al. |
| 7,798,386 B2 | 9/2010 | Schall et al. |
| 7,803,152 B2 | 9/2010 | Honda et al. |
| 7,806,891 B2 | 10/2010 | Nowlin et al. |
| 7,810,693 B2 | 10/2010 | Broehl et al. |
| D627,066 S | 11/2010 | Romero |
| 7,824,401 B2 | 11/2010 | Manzo et al. |
| 7,837,699 B2 | 11/2010 | Yamada et al. |
| 7,846,155 B2 | 12/2010 | Houser et al. |
| 7,854,735 B2 | 12/2010 | Houser et al. |
| D631,155 S | 1/2011 | Peine et al. |
| 7,861,906 B2 | 1/2011 | Doll et al. |
| 7,876,030 B2 | 1/2011 | Taki et al. |
| D631,965 S | 2/2011 | Price et al. |
| 7,892,606 B2 | 2/2011 | Thies et al. |
| 7,901,423 B2 | 3/2011 | Stulen et al. |
| 7,905,881 B2 | 3/2011 | Masuda et al. |
| 7,922,651 B2 | 4/2011 | Yamada et al. |
| D637,288 S | 5/2011 | Houghton |
| D638,540 S | 5/2011 | Ijiri et al. |
| 7,959,050 B2 | 6/2011 | Smith et al. |
| 7,959,626 B2 | 6/2011 | Hong et al. |
| 7,976,544 B2 | 7/2011 | McClurken et al. |
| 7,998,157 B2 | 8/2011 | Culp et al. |
| 8,038,693 B2 | 10/2011 | Allen |
| 8,057,498 B2 | 11/2011 | Robertson |
| 8,058,771 B2 | 11/2011 | Giordano et al. |
| 8,061,014 B2 | 11/2011 | Smith et al. |
| 8,089,197 B2 | 1/2012 | Rinner et al. |
| 8,142,461 B2 | 3/2012 | Houser et al. |
| 8,152,825 B2 | 4/2012 | Madan et al. |
| 8,157,145 B2 | 4/2012 | Shelton, IV et al. |
| 8,162,966 B2 | 4/2012 | Connor et al. |
| 8,177,800 B2 | 5/2012 | Spitz et al. |
| 8,182,502 B2 | 5/2012 | Stulen et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,502 B2 | 6/2012 | Smith et al. |
| 8,226,675 B2 | 7/2012 | Houser et al. |
| 8,236,019 B2 | 8/2012 | Houser |
| 8,236,020 B2 | 8/2012 | Smith et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,287,485 B2 | 10/2012 | Kimura et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,338,726 B2 | 12/2012 | Palmer et al. |
| 8,372,101 B2 | 2/2013 | Smith et al. |
| 8,377,059 B2 | 2/2013 | Deville et al. |
| 8,377,085 B2 | 2/2013 | Smith et al. |
| 8,418,349 B2 | 4/2013 | Smith et al. |
| 8,439,939 B2 | 5/2013 | Deville et al. |
| 8,535,340 B2 | 9/2013 | Allen |
| 8,535,341 B2 | 9/2013 | Allen |
| 2001/0025183 A1 | 9/2001 | Shahidi et al. |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0019649 A1 | 2/2002 | Sikora et al. |
| 2002/0022836 A1 | 2/2002 | Goble et al. |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0156466 A1 | 10/2002 | Sakurai et al. |
| 2002/0156493 A1 | 10/2002 | Houser et al. |
| 2003/0036705 A1 | 2/2003 | Hare et al. |
| 2003/0055443 A1 | 3/2003 | Spotnitz |
| 2003/0204199 A1 | 10/2003 | Novak et al. |
| 2003/0212332 A1 | 11/2003 | Fenton et al. |
| 2003/0212422 A1 | 11/2003 | Fenton et al. |
| 2003/0229344 A1 | 12/2003 | Dycus et al. |
| 2004/0030254 A1 | 2/2004 | Babaev |
| 2004/0047485 A1 | 3/2004 | Sherrit et al. |

(56) References Cited

U.S. PATENT DOCUMENTS

| | | |
|---|---|---|
| 2004/0054364 A1 | 3/2004 | Aranyi et al. |
| 2004/0092921 A1 | 5/2004 | Kadziauskas et al. |
| 2004/0097919 A1 | 5/2004 | Wellman et al. |
| 2004/0097996 A1 | 5/2004 | Rabiner et al. |
| 2004/0176686 A1 | 9/2004 | Hare et al. |
| 2004/0199193 A1 | 10/2004 | Hayashi et al. |
| 2004/0204728 A1* | 10/2004 | Haefner ............ 606/169 |
| 2004/0260300 A1 | 12/2004 | Gorensek et al. |
| 2005/0021065 A1 | 1/2005 | Yamada et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0096683 A1 | 5/2005 | Ellins et al. |
| 2005/0143769 A1 | 6/2005 | White et al. |
| 2005/0149108 A1 | 7/2005 | Cox |
| 2005/0165345 A1 | 7/2005 | Laufer et al. |
| 2005/0177184 A1 | 8/2005 | Easley |
| 2005/0192610 A1 | 9/2005 | Houser et al. |
| 2005/0209620 A1 | 9/2005 | Du et al. |
| 2005/0261581 A1 | 11/2005 | Hughes et al. |
| 2005/0261588 A1 | 11/2005 | Makin et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0063130 A1 | 3/2006 | Hayman et al. |
| 2006/0066181 A1 | 3/2006 | Bromfield et al. |
| 2006/0079876 A1 | 4/2006 | Houser et al. |
| 2006/0079878 A1 | 4/2006 | Houser |
| 2006/0084963 A1 | 4/2006 | Messerly |
| 2006/0095046 A1 | 5/2006 | Trieu et al. |
| 2006/0190034 A1 | 8/2006 | Nishizawa et al. |
| 2006/0206115 A1 | 9/2006 | Schomer et al. |
| 2006/0211943 A1 | 9/2006 | Beaupre |
| 2006/0235306 A1 | 10/2006 | Cotter et al. |
| 2006/0253050 A1* | 11/2006 | Yoshimine et al. ............ 601/2 |
| 2006/0264809 A1 | 11/2006 | Hansmann et al. |
| 2007/0016235 A1 | 1/2007 | Tanaka et al. |
| 2007/0016236 A1 | 1/2007 | Beaupre |
| 2007/0055228 A1 | 3/2007 | Berg et al. |
| 2007/0056596 A1 | 3/2007 | Fanney et al. |
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0106317 A1 | 5/2007 | Shelton, IV et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0162050 A1 | 7/2007 | Sartor |
| 2007/0173872 A1 | 7/2007 | Neuenfeldt |
| 2007/0185380 A1 | 8/2007 | Kucklick |
| 2007/0219481 A1 | 9/2007 | Babaev |
| 2007/0239028 A1 | 10/2007 | Houser et al. |
| 2007/0249941 A1 | 10/2007 | Salehi et al. |
| 2007/0260234 A1 | 11/2007 | McCullagh et al. |
| 2007/0265560 A1 | 11/2007 | Soltani et al. |
| 2007/0275348 A1 | 11/2007 | Lemon |
| 2007/0282335 A1 | 12/2007 | Young et al. |
| 2007/0287933 A1 | 12/2007 | Phan et al. |
| 2008/0009848 A1 | 1/2008 | Paraschiv et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0082039 A1 | 4/2008 | Babaev |
| 2008/0082098 A1 | 4/2008 | Tanaka et al. |
| 2008/0125768 A1 | 5/2008 | Tahara et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188878 A1 | 8/2008 | Young |
| 2008/0200940 A1 | 8/2008 | Eichmann et al. |
| 2008/0208231 A1 | 8/2008 | Ota et al. |
| 2008/0234709 A1 | 9/2008 | Houser |
| 2008/0234710 A1 | 9/2008 | Neurohr et al. |
| 2008/0243106 A1 | 10/2008 | Coe et al. |
| 2008/0245371 A1 | 10/2008 | Gruber |
| 2008/0249553 A1 | 10/2008 | Gruber et al. |
| 2008/0262490 A1 | 10/2008 | Williams |
| 2008/0281200 A1 | 11/2008 | Voic et al. |
| 2008/0287948 A1 | 11/2008 | Newton et al. |
| 2009/0030311 A1 | 1/2009 | Stulen et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036912 A1 | 2/2009 | Wiener et al. |
| 2009/0036913 A1 | 2/2009 | Wiener et al. |
| 2009/0036914 A1 | 2/2009 | Houser |
| 2009/0048537 A1 | 2/2009 | Lydon et al. |
| 2009/0054886 A1 | 2/2009 | Yachi et al. |
| 2009/0054894 A1 | 2/2009 | Yachi |
| 2009/0076506 A1 | 3/2009 | Baker |
| 2009/0082716 A1 | 3/2009 | Akahoshi |
| 2009/0105750 A1 | 4/2009 | Price et al. |
| 2009/0118802 A1 | 5/2009 | Mioduski et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0143806 A1 | 6/2009 | Witt et al. |
| 2009/0270853 A1 | 10/2009 | Yachi et al. |
| 2009/0270899 A1 | 10/2009 | Carusillo et al. |
| 2009/0318945 A1 | 12/2009 | Yoshimine et al. |
| 2009/0327715 A1 | 12/2009 | Smith et al. |
| 2010/0004668 A1 | 1/2010 | Smith et al. |
| 2010/0004669 A1 | 1/2010 | Smith et al. |
| 2010/0016785 A1 | 1/2010 | Takuma |
| 2010/0030248 A1 | 2/2010 | Palmer et al. |
| 2010/0036370 A1 | 2/2010 | Mirel et al. |
| 2010/0069940 A1 | 3/2010 | Miller et al. |
| 2010/0158307 A1 | 6/2010 | Kubota et al. |
| 2010/0187283 A1 | 7/2010 | Crainich et al. |
| 2010/0193567 A1 | 8/2010 | Scheib et al. |
| 2010/0228264 A1 | 9/2010 | Robinson et al. |
| 2010/0234906 A1 | 9/2010 | Koh |
| 2010/0268211 A1 | 10/2010 | Manwaring et al. |
| 2010/0298743 A1 | 11/2010 | Nield et al. |
| 2010/0298851 A1 | 11/2010 | Nield |
| 2010/0331869 A1 | 12/2010 | Voegele et al. |
| 2010/0331870 A1 | 12/2010 | Wan et al. |
| 2010/0331871 A1 | 12/2010 | Nield et al. |
| 2010/0331872 A1 | 12/2010 | Houser et al. |
| 2011/0009850 A1 | 1/2011 | Main et al. |
| 2011/0015627 A1 | 1/2011 | DiNardo et al. |
| 2011/0015631 A1 | 1/2011 | Wiener et al. |
| 2011/0015660 A1 | 1/2011 | Wiener et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2011/0087256 A1 | 4/2011 | Wiener et al. |
| 2011/0196286 A1 | 8/2011 | Robertson et al. |
| 2011/0196287 A1 | 8/2011 | Robertson et al. |
| 2011/0196398 A1 | 8/2011 | Robertson et al. |
| 2011/0196399 A1 | 8/2011 | Robertson et al. |
| 2011/0196400 A1 | 8/2011 | Robertson et al. |
| 2011/0196401 A1 | 8/2011 | Robertson et al. |
| 2011/0196402 A1 | 8/2011 | Robertson et al. |
| 2011/0196403 A1 | 8/2011 | Robertson et al. |
| 2011/0196404 A1 | 8/2011 | Dietz et al. |
| 2011/0196405 A1 | 8/2011 | Dietz |
| 2011/0288452 A1 | 11/2011 | Houser et al. |
| 2012/0029546 A1 | 2/2012 | Robertson |
| 2012/0059289 A1 | 3/2012 | Nield et al. |

(56) References Cited

U.S. PATENT DOCUMENTS

| | | |
|---|---|---|
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0083783 A1 | 4/2012 | Davison et al. |
| 2012/0083784 A1 | 4/2012 | Davison et al. |
| 2012/0132450 A1 | 5/2012 | Timm et al. |
| 2012/0138660 A1 | 6/2012 | Shelton, IV |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0203257 A1 | 8/2012 | Stulen et al. |
| 2012/0205421 A1 | 8/2012 | Shelton, IV |
| 2012/0209289 A1 | 8/2012 | Duque et al. |
| 2012/0210223 A1 | 8/2012 | Eppolito |
| 2012/0211546 A1 | 8/2012 | Shelton, IV |
| 2012/0259353 A1 | 10/2012 | Houser et al. |
| 2012/0265196 A1 | 10/2012 | Turner et al. |
| 2012/0269676 A1 | 10/2012 | Houser et al. |
| 2012/0289984 A1 | 11/2012 | Houser et al. |
| 2012/0310262 A1 | 12/2012 | Messerly et al. |
| 2012/0310263 A1 | 12/2012 | Messerly et al. |
| 2012/0310264 A1 | 12/2012 | Messerly et al. |
| 2012/0323265 A1 | 12/2012 | Stulen |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0123822 A1 | 5/2013 | Wellman et al. |

FOREIGN PATENT DOCUMENTS

| | | |
|---|---|---|
| CN | 1694649 A | 11/2005 |
| CN | 1922563 A | 2/2007 |
| CN | 1951333 A | 4/2007 |
| CN | 101040799 A | 9/2007 |
| EP | 0171967 A2 | 2/1986 |
| EP | 0443256 A1 | 8/1991 |
| EP | 0456470 A1 | 11/1991 |
| EP | 0482195 B1 | 1/1996 |
| EP | 0612570 B1 | 6/1997 |
| EP | 0908148 B1 | 1/2002 |
| EP | 0908155 B1 | 6/2003 |
| EP | 1199044 B1 | 12/2005 |
| EP | 1199043 B1 | 3/2006 |
| EP | 1433425 B1 | 6/2006 |
| EP | 1844720 A1 | 10/2007 |
| EP | 1862133 A1 | 12/2007 |
| EP | 1199045 B1 | 6/2008 |
| EP | 1974771 A1 | 10/2008 |
| EP | 1498082 B1 | 12/2008 |
| EP | 1832259 B1 | 6/2009 |
| EP | 2074959 A1 | 7/2009 |
| EP | 2298154 A2 | 3/2011 |
| GB | 2032221 A | 4/1980 |
| GB | 2379878 B | 11/2004 |
| GB | 2447767 B | 8/2011 |
| JP | 62-2292153 A | 12/1987 |
| JP | 63-315049 A | 12/1988 |
| JP | 02-71510 U | 5/1990 |
| JP | 04-25707 U | 2/1992 |
| JP | 4-30508 U | 3/1992 |
| JP | 6-104503 A | 4/1994 |
| JP | 6-507081 A | 8/1994 |
| JP | H 7-508910 A | 10/1995 |
| JP | 7-308323 A | 11/1995 |
| JP | 8-24266 A | 1/1996 |
| JP | 8-275951 A | 10/1996 |
| JP | H 09-503146 A | 3/1997 |
| JP | 10-295700 A | 11/1998 |
| JP | 11-253451 A | 9/1999 |
| JP | 2000-041991 A | 2/2000 |
| JP | 2000-070279 A | 3/2000 |
| JP | 2001-309925 A | 11/2001 |
| JP | 2002-186901 A | 7/2002 |
| JP | 2002-263579 A | 9/2002 |
| JP | 2003-510158 A | 3/2003 |
| JP | 2003-126110 A | 5/2003 |
| JP | 2003-310627 A | 5/2003 |
| JP | 2003-339730 A | 12/2003 |
| JP | 2005027026 A | 1/2005 |
| JP | 2005-066316 A | 3/2005 |
| JP | 2005-074088 A | 3/2005 |
| JP | 2005-534451 A | 11/2005 |
| JP | 2006-158525 A | 6/2006 |
| JP | 2006217716 A | 8/2006 |
| JP | 2008-508065 A | 3/2008 |
| JP | 2008-119250 A | 5/2008 |
| JP | 2009-511206 A | 3/2009 |
| WO | WO 92/22259 A2 | 12/1992 |
| WO | WO 93/14708 A1 | 8/1993 |
| WO | WO 94/21183 A1 | 9/1994 |
| WO | WO 95/09572 A1 | 4/1995 |
| WO | WO 98/26739 A1 | 6/1998 |
| WO | WO 98/37815 A1 | 9/1998 |
| WO | WO 2005/122917 A1 | 9/1998 |
| WO | WO 01/54590 A1 | 8/2001 |
| WO | WO 01/95810 A2 | 12/2001 |
| WO | WO 2004/037095 A2 | 5/2004 |
| WO | WO 2006/012797 A1 | 2/2006 |
| WO | WO 2006/042210 A2 | 4/2006 |
| WO | WO 2006/058223 A2 | 6/2006 |
| WO | WO 2006/063199 A2 | 6/2006 |
| WO | WO 2006/083988 A1 | 8/2006 |
| WO | WO 2006/129465 A1 | 12/2006 |
| WO | WO 2007/008710 A2 | 1/2007 |
| WO | WO 2007/047531 A2 | 4/2007 |
| WO | WO 2007/143665 A2 | 12/2007 |
| WO | WO 2008/016886 A2 | 2/2008 |
| WO | WO 2008/042021 A1 | 4/2008 |
| WO | WO 2008/130793 A1 | 10/2008 |
| WO | WO 2009/018406 A2 | 2/2009 |
| WO | WO 2009/027065 A1 | 3/2009 |
| WO | WO 2011/144911 A1 | 11/2011 |

OTHER PUBLICATIONS

Gooch et al., "Recommended Infection-Control Practices for Dentistry, 1993," Published; May 28, 1993; [retrieved on Aug. 23, 2008]. Retrieved from the internet: URL: http//wonder.cdc.gov/wonder/prevguid/p0000191/p0000191.asp (15 pages).

International Search Report for PCT/US08/57325, Sep. 3, 2008 (4 pages).

Australian Patent Examination Report No. 1, Application No. 2008231160, dated Jul. 24, 2012 (3 pages).

*Technology Overview*, printed from www.harmonicscalpel.com Internet site, website accessed on Jun. 13, 2007 (3 pages).

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.

AST Products, Inc., "Principles of Video Contact Angle Analysis," 20 pages, (2006).

Lim et al., "A Review of Mechanism Used in Laparoscopic Surgical Instruments," Mechanism and Machine Theory, vol. 38, pp. 1133-1147, (2003).

Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).

Incropera et al., Fundamentals of Heat and Mass Transfer, Wiley, New York (1990). (Book—not attached).

F. A. Duck, "Optical Properties of Tissue Including Ultraviolet and Infrared Radiation," pp. 43-71 in *Physical Properties of Tissue* (1990).

Orr et al., "Overview of Bioheat Transfer," pp. 367-384 in Optical-Thermal Response of Laser-Irradiated Tissue, A. J. Welch and M. J. C. van Gemert, eds., Plenum, New York (1995).

(56) References Cited

OTHER PUBLICATIONS

Campbell et al, "Thermal Imaging in Surgery," p. 19-3, in *Medical Infrared Imaging*, N. A. Diakides and J. D. Bronzino, Eds. (2008).
U.S. Appl. No. 29/404,676, filed Oct. 24, 2011.
U.S. Appl. No. 13/448,175, filed Apr. 16, 2012.
U.S. Appl. No. 13/151,181, filed Jun. 2, 2011.
U.S. Appl. No. 13/369,561, filed Feb. 9, 2012.
U.S. Appl. No. 13/369,569, filed Feb. 9, 2012.
U.S. Appl. No. 13/369,578, filed Feb. 9, 2012.
U.S. Appl. No. 13/369,584, filed Feb. 9, 2012.
U.S. Appl. No. 13/369,588, filed Feb. 9, 2012.
U.S. Appl. No. 13/369,594, filed Feb. 9, 2012.
U.S. Appl. No. 13/369,601 filed Feb. 9, 2012.
U.S. Appl. No. 13/369,609, filed Feb. 9, 2012.
U.S. Appl. No. 13/369,629, filed Feb. 9, 2012.
U.S. Appl. No. 13/369,666, filed Feb. 9, 2012.
European Search Report for 08743998.0, Nov. 16, 2012 (7 pages).
U.S. Appl. No. 13/584,020, filed Aug. 13, 2012.
U.S. Appl. No. 13/584,445, filed Aug. 13, 2012.
U.S. Appl. No. 13/849,627, filed Mar. 25, 2013.

* cited by examiner

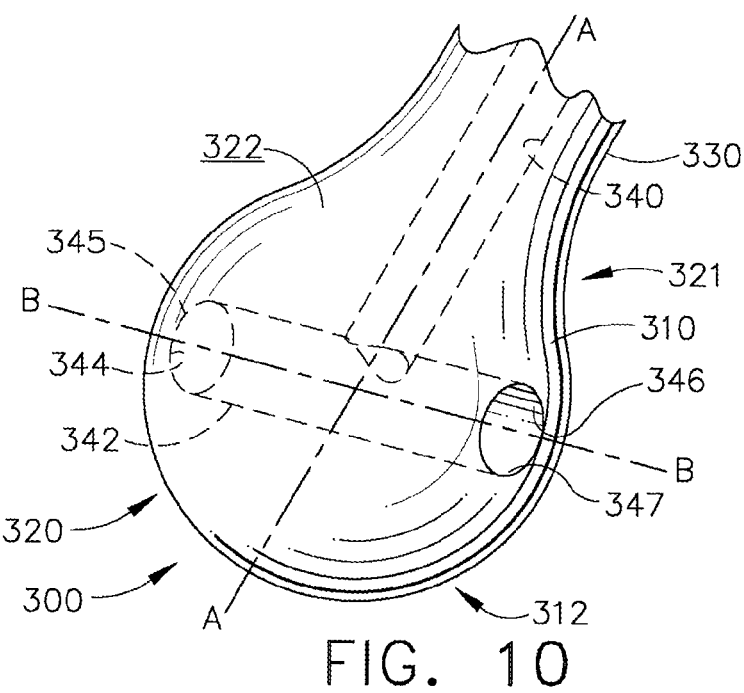
FIG. 10
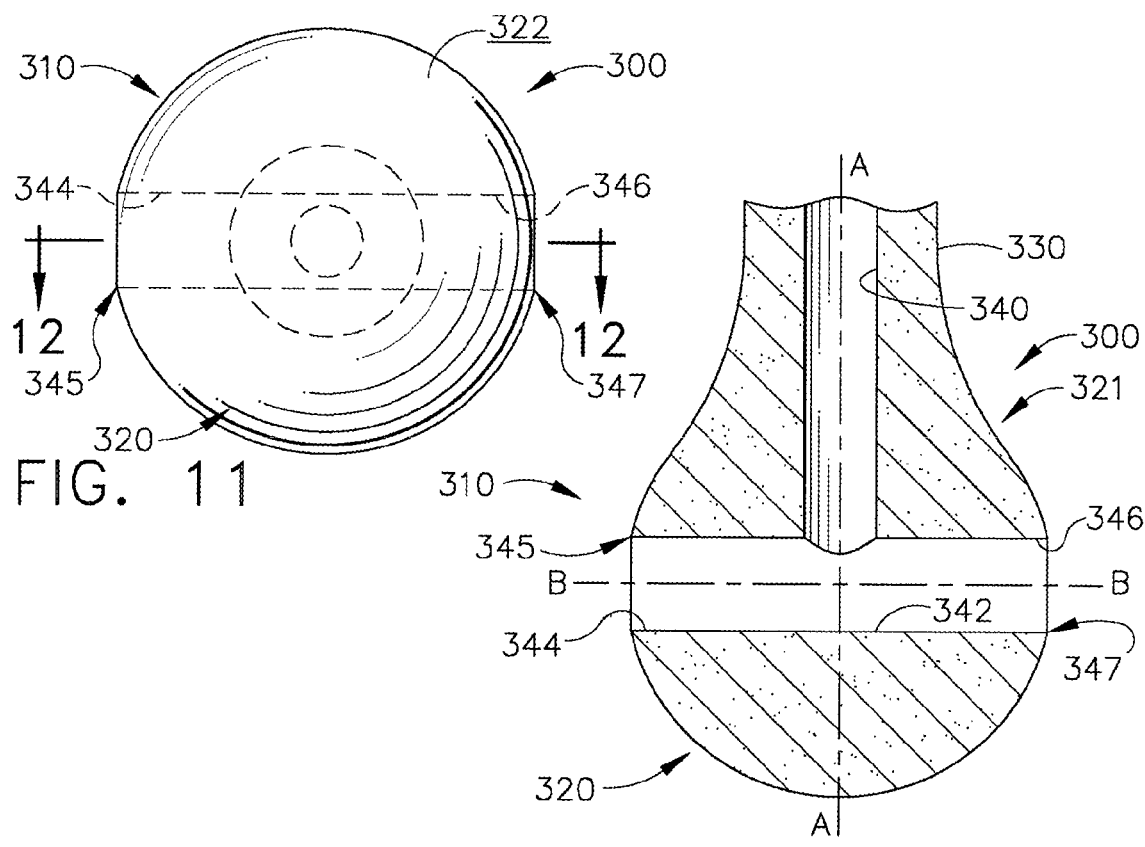
FIG. 11
FIG. 12

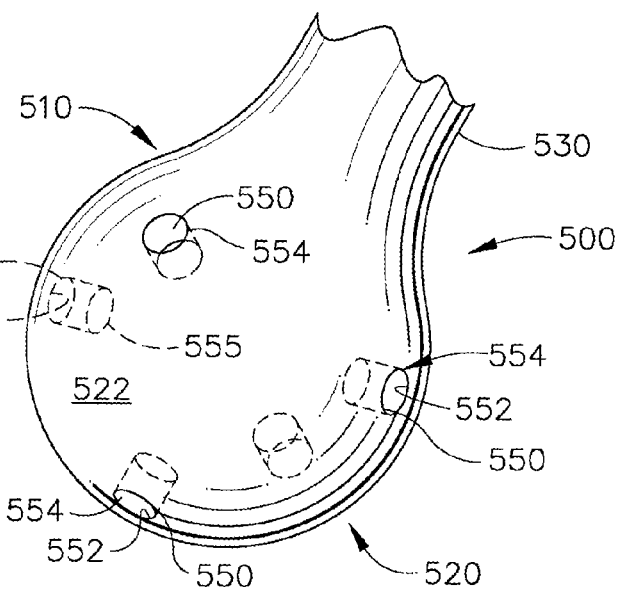
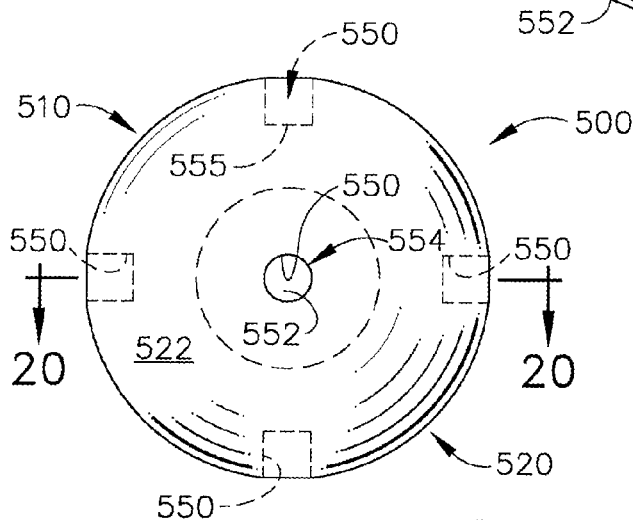
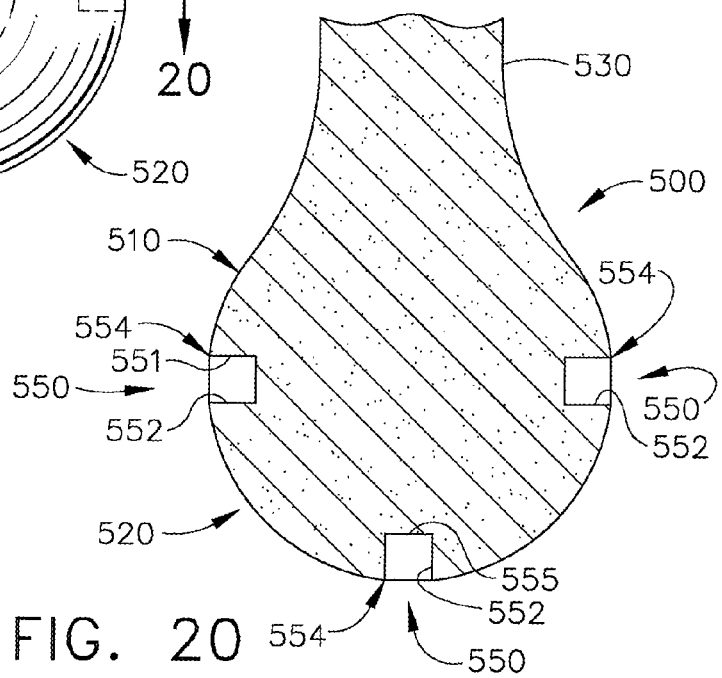

ULTRASONIC SURGICAL INSTRUMENT AND CARTILAGE AND BONE SHAPING BLADES THEREFOR

CROSS-REFERENCE TO RELATED APPLICATIONS

The present non-provisional application is a divisional application claiming priority from U.S. patent application Ser. No. 12/732,702, now U.S. Pat. No. 8,236,019, entitled ULTRASONIC SURGICAL INSTRUMENT AND CARTILAGE AND BONE SHAPING BLADES THEREFOR, filed Mar. 26, 2010, which is a divisional application claiming priority from U.S. patent application Ser. No. 11/726,621, now Abandoned, entitled ULTRASONIC SURGICAL INSTRUMENT AND CARTILAGE AND BONE SHAPING BLADES THEREFOR, filed Mar. 22, 2007 the entire disclosures of which are incorporated by reference herein.

The present application is related to the following commonly-owned U.S. patent applications which are hereby incorporated by reference in their entirety:

(1) U.S. patent application Ser. No. 11/726,620, entitled SURGICAL INSTRUMENTS, filed Mar. 22, 2007;
(2) U.S. patent application Ser. No. 11/726,625, entitled ULTRASONIC SURGICAL INSTRUMENTS, filed Mar. 22, 2007; and
(3) U.S. patent application Ser. No. 11/726,760, entitled SURGICAL INSTRUMENTS, filed Mar. 22, 2007.

FIELD OF THE INVENTION

The present invention relates, in general, to ultrasonic surgical instruments and, more particularly, to ultrasonic surgical instruments and blades configured for removing bone and/or shaping cartilage.

BACKGROUND OF THE INVENTION

During various orthopedic surgical procedures, it is often necessary to remove small layers of cortical bone. Several different tools have been developed to accomplish this task and for preparing and/or shaping bone surfaces. For example, mallets are often used to apply an impacting force on a medical tool, such as a chisel, to remove pieces of bone. While mallets are somewhat effective, the impacting force must be carefully applied to avoid removal of too much bone or the inadvertent removal of a wrong piece of bone. Moreover, the force applied to the chisel must be applied in a sufficiently accurate manner to avoid damage to adjacent tissues and/or organs.

Other surgical tools known as burrs have also been developed for removing layers of cortical bone and shaping bone and cartilage. Such devices, however, generally must be employed with high levels of precision to ensure that only the desired amount of bone is removed and the surrounding tissues are not undesirably damaged or traumatized. These burrs and similar instruments, however, do not provide a means for controlling bleeding and tend to leave the treated tissue with a roughened surface. In an effort to address those problems, radio frequency-based devices were developed.

Radio frequency-based devices enable surgeons to remove, modulate, or sculpt soft tissue while simultaneously sealing blood vessels. They work particularly well on connective tissue, which is primarily comprised of collagen and which contracts when contacted by heat. However, such radio frequency-based devices can create undesirable deep thermal injury in the tissue.

Other instruments that have been developed for effectively cutting and coagulating organic tissue employ mechanical vibrations that are transmitted to a surgical end-effector at ultrasonic frequencies. Ultrasonic vibrations, when transmitted to organic tissue at suitable energy levels and using a suitable end-effector, may be used to cut, dissect, elevate or cauterize tissue or to separate muscle tissue off bone. Ultrasonic instruments utilizing solid core technology are particularly advantageous because of the amount of ultrasonic energy that may be transmitted from the ultrasonic transducer, through a waveguide, to the surgical end-effector.

Activating or exciting the end-effector (e.g., cutting blade) of such instruments at ultrasonic frequencies induces longitudinal vibratory movement that generates localized heat within adjacent tissue, facilitating both cutting and coagulation. Because of the nature of ultrasonic instruments, a particular ultrasonically actuated end-effector may be designed to perform numerous functions, including, for example, cutting and coagulation.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end-effector via an ultrasonic waveguide extending from the transducer section to the surgical end-effector. The waveguides and end-effectors are designed to resonate at the same frequency as the transducer. Therefore, when an end-effector is attached to a transducer the overall system frequency is the same frequency as the transducer itself. Nevertheless, those skilled in the art will appreciate that the system may be designed where the transducer and the blade resonate at different frequencies and when joined the system resonates at a desired frequency.

The amplitude of the longitudinal ultrasonic vibration at the tip, d, of the end-effector behaves as a simple sinusoid at the resonant frequency as given by:

$$d = A \sin(\omega t)$$

where:
$\omega$=the radian frequency which equals $2\pi$ times the cyclic frequency, f and
A=the zero-to-peak amplitude.
The longitudinal excursion is defined as the peak-to-peak (p-t-p) amplitude, which is just twice the amplitude of the sine wave or 2A.

Over the years, a variety of different ultrasonic blade configurations have been developed. Blades that tend to work well from a coagulation standpoint (and hence change tissue into a sticky coagulum that can be readily reshaped) do not tend to cut extremely well. Some of those blades generally have spherically-shaped body with a substantially smooth outer surface. FIGS. 2 and 3 depict a spherically-shaped blade 10 of this type that has been used in the past. Such blade design, while effective from a coagulation standpoint, is not particularly well-suited for bone removal or tissue reshaping applications due to its shape. Other existing blades that are better adapted for cutting tissue, are not as well-suited to coagulate and reshape tissue. These problems can be further exacerbated in arthroscopic procedures that afford limited access to the target tissue or bone and where the blade must work in an aqueous environment.

It would, therefore, be advantageous to design a harmonic surgical instrument for shaping either soft tissues such as cartilage or meniscus or for decorticating bone. It would be further advantageous to design a harmonic surgical instrument that can be used to decorticate and aspirate bone and also facilitate spot coagulation of tissue as well as tissue reshaping. Various embodiments of the present invention incorporate improvements to known ultrasonic instruments to provide these advantages. The foregoing discussion is intended only to illustrate some of the shortcomings present in the field of the invention at the time, and should not be taken as a disavowal of claim scope.

SUMMARY

In one aspect of the invention, there is provided a surgical instrument that comprises an ultrasonic surgical blade that includes a blade body that has a treatment region. In various embodiments, at least one indentation is formed in the treatment region of the blade body wherein each indentation forms a tissue cutting edge with an outer surface of the blade body.

In another general aspect of various embodiments of the present invention there is provided an ultrasonic surgical blade. In various embodiments, the blade has a blade body that includes a substantially spherically-shaped treatment region. At least one substantially sharp edge can be formed on at least a portion of the spherically-shaped treatment region.

In still another general aspect of various embodiments of the present invention there is provided an ultrasonic surgical instrument comprising an ultrasonic transmission member that has a proximal end and a distal end and an ultrasonically actuated blade that is attached to the distal end of the transmission member. In various embodiments, the blade has a blade body that has a treatment region. At least one indentation can be formed in the treatment region of the blade body. Each indentation may form a tissue cutting edge with an outer surface of the blade body.

These and other objects and advantages of the present invention shall be made apparent from the accompanying drawings and the description thereof.

BRIEF DESCRIPTION OF THE FIGURES

The novel features of the various embodiments of the invention are set forth with particularity in the appended claims. The various embodiments of the invention, however, both as to organization and methods of operation, together with further objects and advantages thereof, may best be understood by reference to the following description, taken in conjunction with the accompanying drawings in which:

FIG. 10 is a perspective view of a portion of another ultrasonic surgical blade embodiment of the present invention;

FIG. 11 is an elevational view of a distal end of the ultrasonic surgical blade of FIG. 10;

FIG. 12 is a cross-sectional view of the portion of the ultrasonic blade depicted in FIGS. 10 and 11 taken along line 12-12 in FIG. 11;

FIG. 18 is a perspective view of a portion of another ultrasonic surgical blade embodiment of the present invention;

FIG. 19 is an elevational view of a distal end of the ultrasonic surgical blade of FIG. 18;

FIG. 20 is a cross-sectional view of the portion of the ultrasonic blade depicted in FIGS. 18 and 19 taken along line 20-20 in FIG. 19;

DETAILED DESCRIPTION

Figure 1:
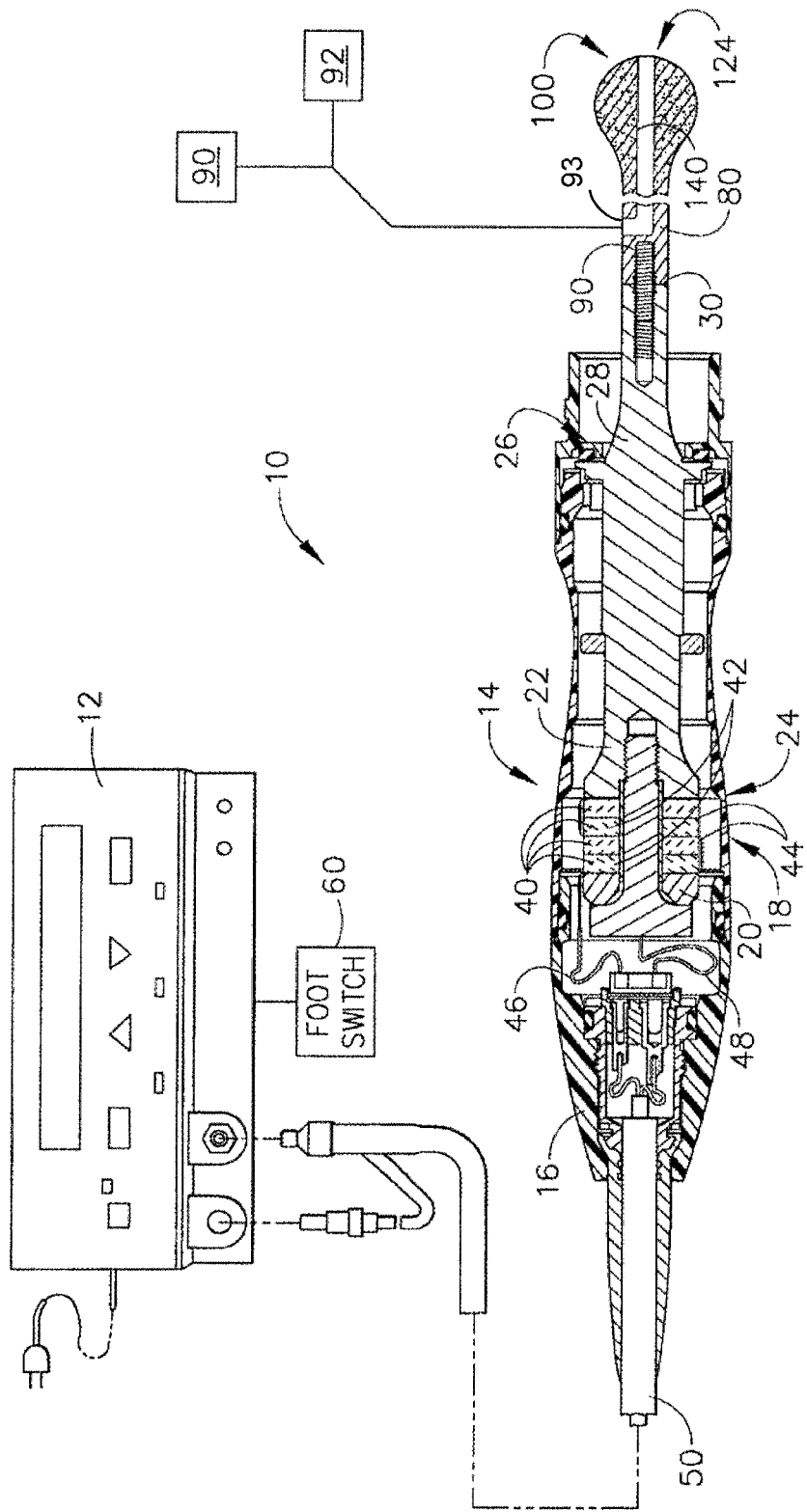
FIG. 1 is a partial cross-sectional view of a surgical instrument of various embodiments of the present invention.
Figure 2:
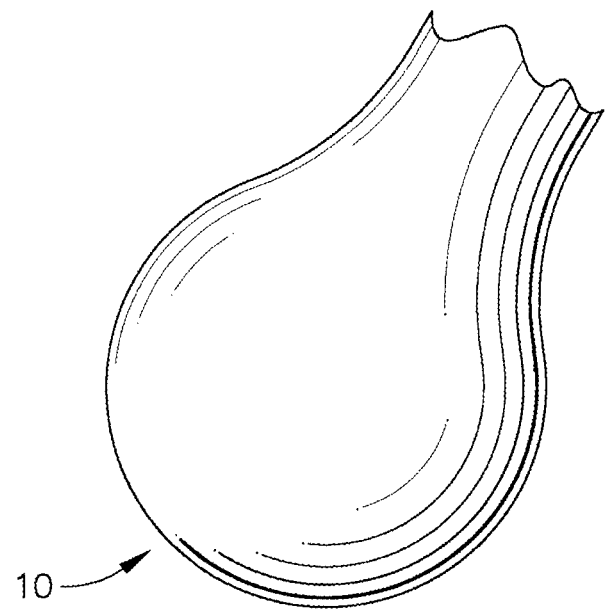
FIG. 2 is a partial perspective view of a portion of a prior ultrasonic surgical blade.
Figure 3:
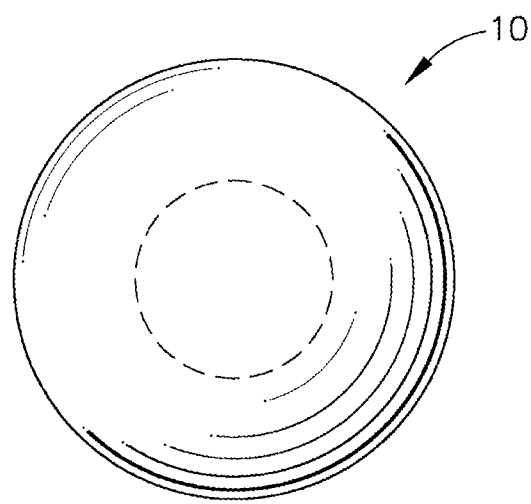
FIG. 3 is an elevational view of the distal end of the prior blade depicted in FIG. 2.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, the surgical instrument and blade configurations disclosed below are illustrative only and not meant to limit the scope or application of the invention. Furthermore, unless otherwise indicated, the terms and expressions employed herein have been chosen for the purpose of describing the illustrative embodiments of the present invention for the convenience of the reader and are not for the purpose of limiting the invention.

Various embodiments of the present invention relate, in general, to ultrasonic surgical blades for use with ultrasonic surgical instruments and, more particularly, to ultrasonic surgical blades and instruments for improved bone and tissue removal, aspiration, and coagulation features. A blade according to various embodiments of the present invention may be of particular benefit in orthopedic procedures wherein it is desirable to remove cortical bode and/or tissue while controlling bleeding. A variety of different blade configurations are disclosed which may be useful for both open and laparoscopic applications.

Examples of ultrasonic surgical instruments are disclosed in U.S. Pat. Nos. 5,322,055 and 5,954,736 and in combination with ultrasonic blades and surgical instruments as, for example, disclosed in U.S. Pat. Nos. 6,309,400 B2, 6,278,218 B1, 6,283,981 B1, and 6,325,811 B1 all of which are incorporated in their entirety by reference herein. These references disclose ultrasonic surgical instrument design and blade designs where a longitudinal anti-node of the blade is excited. Because of asymmetry or asymmetries, these blades exhibit transverse and/or torsional motion where the characteristic "wavelength" of this non-longitudinal motion is less than that of the general longitudinal motion of the blade and its extender portion. Therefore, the wave shape of the non-longitudinal motion will present nodal positions of transverse/torsional motion along the tissue effector while the net motion of the active blade along its tissue effector is non-zero (i.e. will have at least longitudinal motion along the length extending from its distal end, an antinode of longitudinal motion, to the first nodal position of longitudinal motion that is proximal to the tissue effector portion). Those of ordinary skill in the art will also appreciate that the combination of transverse and/or torsional motions in combination with the longitudinal motion could augment the cutting action. Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

FIG. 1 illustrates ultrasonic system 10 comprising an ultrasonic signal generator 12 with ultrasonic transducer 14, hand piece housing 16, and blade 100 in accordance with the present invention. The ultrasonic transducer 14, which is known as a "Langevin stack", generally includes a transduction portion 18, a first resonator or end-bell 20, and a second resonator or fore-bell 22, and ancillary components. The ultrasonic transducer 14 is preferably an integral number of one-half system wavelengths (nλ/2) in length as will be described in more detail later. An acoustic assembly 24 includes the ultrasonic transducer 14, mount 26, velocity transformer 28 and surface 30.

The distal end of end-bell 20 is connected to the proximal end of transduction portion 18, and the proximal end of fore-bell 22 is connected to the distal end of transduction portion 18. Fore-bell 22 and end-bell 20 have a length determined by a number of variables, including the thickness of the transduction portion 18, the density and modulus of elasticity of the material used to manufacture end-bell 20 and fore-bell 22, and the resonant frequency of the ultrasonic transducer 14. The fore-bell 22 may be tapered inwardly from its proximal end to its distal end to amplify the ultrasonic vibration amplitude as velocity transformer 28, or alternately may have no amplification.

The transducer may be constructed of one or more piezoelectric or magnetostrictive elements in the instrument hand piece. Ultrasonic vibration is induced in the surgical end-effector by, for example, electrically exciting a transducer which may be constructed of one or more piezoelectric or magnetostrictive elements in the instrument hand-piece. Vibrations generated by the transducer section are transmitted to the surgical end-effector via an ultrasonic waveguide extending from the transducer section to the surgical end-effector.

In the illustrated embodiment, the transducer is constructed with piezoelectric elements 40. The piezoelectric elements 40 may be fabricated from any suitable material, such as, for example, lead zirconate-titanate, lead meta-niobate, lead titanate, or other piezoelectric crystal material. Each of the positive electrodes 42, negative electrodes 44, and piezoelectric elements 40 has a bore extending through the center. The positive and negative electrodes 42 and 44 are electrically coupled to wires 46 and 48, respectively. Wires 46 and 48 are encased within cable 50 and electrically connectable to ultrasonic signal generator 12 of ultrasonic system 10.

Ultrasonic transducer 14 of the acoustic assembly 24 converts the electrical signal from ultrasonic signal generator 12 into mechanical energy that results in primarily longitudinal vibratory motion of the ultrasonic transducer 14 and blade 100 at ultrasonic frequencies. A suitable generator is available as model number GEN04, from Ethicon Endo-Surgery, Inc., Cincinnati, Ohio. When the acoustic assembly 24 is energized, a vibratory motion standing wave is generated through the acoustic assembly 24. The amplitude of the vibratory motion at any point along the acoustic assembly 24 may depend upon the location along the acoustic assembly 24 at which the vibratory motion is measured. A minimum or zero crossing in the vibratory motion standing wave is generally referred to as a node (i.e., where motion is usually minimal), and an absolute value maximum or peak in the standing wave is generally referred to as an anti-node. The distance between an anti-node and its nearest node is one-quarter wavelength (λ/4).

Wires 46 and 48 transmit the electrical signal from the ultrasonic signal generator 12 to positive electrodes 42 and negative electrodes 44. The piezoelectric elements 40 are energized by an electrical signal supplied from the ultrasonic signal generator 12 in response to a foot switch 60 to produce an acoustic standing wave in the acoustic assembly 24. The electrical signal causes disturbances in the piezoelectric elements 40 in the form of repeated small displacements resulting in large compression forces within the material. The repeated small displacements cause the piezoelectric elements 40 to expand and contract in a continuous manner along the axis of the voltage gradient, producing longitudinal waves of ultrasonic energy. The ultrasonic energy is transmitted through the acoustic assembly 24 to the blade 100.

In order for the acoustic assembly 24 to deliver energy to the blade 100, all components of acoustic assembly 24 must be acoustically coupled to the blade 100. The distal end of the ultrasonic transducer 14 may be acoustically coupled at surface 30 to the proximal end of an ultrasonic waveguide 80 by a threaded connection such as stud 90.

The components of the acoustic assembly 24 are preferably acoustically tuned such that the length of any assembly is an integral number of one-half wavelengths (nλ/2), where the wavelength λ is the wavelength of a pre-selected or operating longitudinal vibration drive frequency $f_d$ of the acoustic assembly 24, and where n is any positive integer. It is also contemplated that the acoustic assembly 24 may incorporate any suitable arrangement of acoustic elements.

In addition, an aspiration transducer may be provided, such as a phaco-emulsifier, includes a central lumen in the transducer to allow for aspiration of tissue and fluids through the back of the transducer. The central lumen may be inserted through an incision and vibrates ultrasonically to liquefy tissue. The emulsified tissue is removed by aspiration via the lumen through the back of the transducer. Modern aspirators also perform irrigation. These irrigation/aspiration instruments have dual passages or lumens, one for irrigation and the other for aspiration. Usually the passages are coaxial, the inner passage being formed by a rigid or semi-rigid cannula, and the outer passage having a distal portion formed by a sleeve which may be resilient. One or more components of the tips are removable from the handpiece of the instrument for selection of an appropriate or desired tip, and for replacement of the tip.

Figure 4:
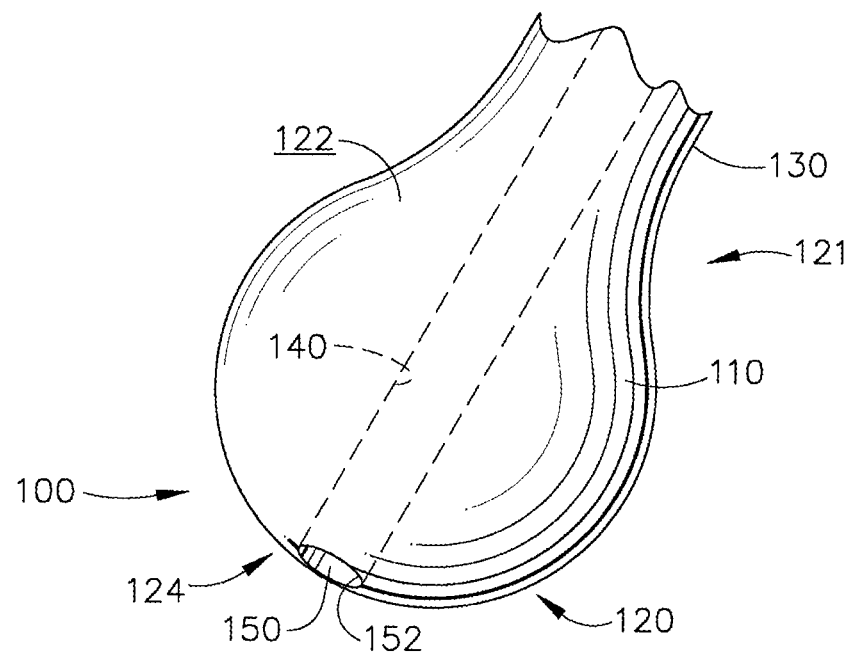
FIG. 4 is a perspective view of a portion of an ultrasonic surgical blade embodiment of the present invention.
Figure 5:
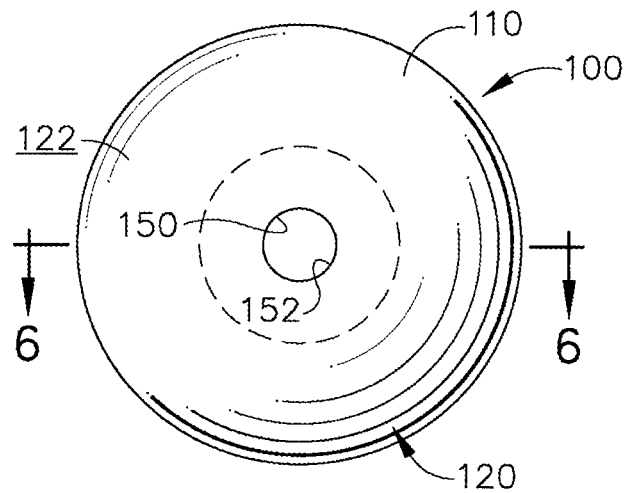
FIG. 5 is an elevational view of a distal end of the ultrasonic surgical blade of FIG. 4.
Figure 6:
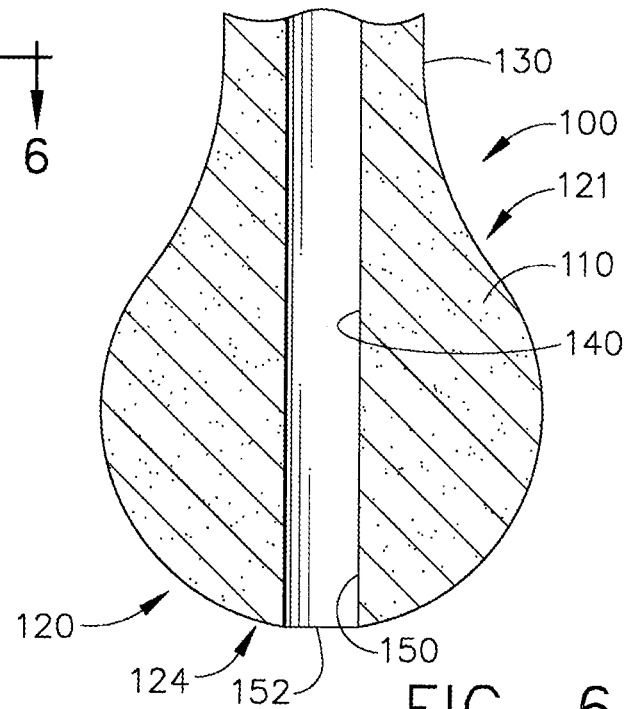
FIG. 6 is a cross-sectional view of the portion of the ultrasonic blade depicted in FIGS. 4 and 5 taken along line 6-6 in FIG. 5.

FIGS. 4-6 illustrate one ultrasonic surgical blade embodiment of the present invention that may be employed with the above-described ultrasonic instrument 10. However, as the present detailed description proceeds, those of ordinary skill in the art will understand that the various ultrasonic surgical blade embodiments that are disclosed herein as well as any equivalent structures thereof could conceivably be effectively used in connection with other known ultrasonic surgical instruments without departing from the spirit and scope of the present invention. Thus, the protection afforded to the various ultrasonic surgical blade embodiments disclosed herein should not be limited to use only in connection with the exemplary ultrasonic surgical instrument described above.

As can be seen in FIGS. 4-6, the ultrasonic surgical blade 100 has a blade body 110 that has a generally smooth exterior surface 122 that is well-suited for coagulation and tissue reshaping applications. The smooth exterior surface is well-suited for coagulation of tissue due to the ability to place a large blunt surface that is ultrasonically active against the tissue. This allows for the transfer of heat without the risk of cutting, allowing the tissue to form into a sticky coagulum that seals vessels. The blade 100 may be fabricated from a material suitable for transmission of ultrasonic energy such as, for example, Ti6 A14V (an alloy of Titanium including Aluminum and Vanadium), Aluminum, Stainless Steel, or other known materials. The blade body 110 may comprise a substantially spherically-shaped treatment region, generally designated as 120, and a neck or transition portion 130 that protrudes from a proximal portion 121 of the treatment region 120. As indicated above, the neck portion 130 may be attached to the waveguide 80 by, for example, a stud, welding, gluing, or other known methods. In alternative embodiments, the neck portion 130 and waveguide 80 may comprise a single unit. The ultrasonic waveguide 80 may, for example, have a length substantially equal to an integral number of one-half system wavelengths ($\lambda/2$). The ultrasonic waveguide 80 may be preferably fabricated from a solid core shaft constructed out of material that propagates ultrasonic energy efficiently, such as titanium alloy (i.e., Ti-6A1-4V) or an aluminum alloy, for example. The ultrasonic waveguide 80 may also be configured to amplify the mechanical vibrations transmitted to the ultrasonic blade 100 as is well known in the art.

In alternative embodiments the ultrasonic transmission waveguide may be fabricated with a hollow core. In other embodiments, the ultrasonic surgical blade may comprise an outer sheath that protects patient tissues from the ultrasonic transmission waveguide. In such embodiment, a lumen may be provided in the longitudinal extending space between the outer sheath and the surgical blade. The lumen may be employed to irrigate or aspirate tissue trough through the lumen located between the blade and the outer sheath.

The ultrasonic blade 100 may have a length substantially equal to an integral multiple of one-half system wavelengths ($\lambda/2$). The distal end of ultrasonic blade 100 is disposed near an antinode in order to provide the maximum longitudinal excursion of the distal end. When the transducer assembly is energized, the distal end 124 of the ultrasonic blade 100 may be configured to move in the range of, for example, approximately 10 to 150 microns peak-to-peak, and preferably in the range of about 30 to 150 100 microns at a predetermined vibrational frequency of 55.5 kHz. The ultrasonic blade 100 may be configured to vibrate with an amplitude at a specified frequency that creates a blade velocity of between 2 meters/sec and 30 meters/sec.

While the treatment region in this exemplary embodiment is substantially spherical in shape, those of ordinary skill in the art will appreciate that the blade body 110 may be provided in other shapes that provide a substantially smooth and rounded outer perimeter. For example, the blade body could comprise a slightly elongated cylinder-like member with a rounded distal end.

Referring to FIG. 1, in various embodiments, an aspiration lumen 140 may be provided through the treatment region 120 and neck portion 130 and be configured to ultimately communicate with a stand alone suction/irrigation module, tower mounted suction 90 and/or irrigation 92 modules (FIG. 1), or an integrated ultrasonic generator/suction/irrigation module in the operating room, for example. It may also be advantageous to integrate suction/irrigation controls (i.e. trumpet valves, etc.) and a means for selecting either suction or irrigation functions within the device handle. An inlet 93 may allow communication between the aspiration lumen 140 and the suction 90 and/or irrigation 92 modules. The inlet 93 may be distal to the transducer 14.

As can be seen in FIGS. 4 and 6, the aspiration lumen 140 can form an opening 150 in the distal end 124 of the treatment region 120. In various embodiments, the opening 150 is defined by a tissue cutting edge 152 formed in the outer surface 122 of the treatment region 120. Cutting edge 152 can be used to cut and reshape tissue and it may also serve as a bearing surface or edge for removing cortical bone. As the tissue and/or bone material is cut away or dislodged by cutting edge 152, the material can be removed from the surgical field through the lumen 140 and the aspiration passage in the surgical instrument. In at least one embodiment, the spherically-shaped treatment region 110 and relative smooth perimetrical outer surface 122 are well-suited for coagulating and reshaping tissue. More particularly, owing to the substantially spherically shaped surface 122, surface 122 can be used to heat and manipulate tissue, for example, without cutting it such that, when the tissue cools, the tissue can maintain its reconfigured shape. The edge 152 may also provide the surgeon with a means for cutting and shaping tissue and dislodging pieces of bone which represents a vast improvement of prior spherically-shaped ultrasonic blades. This embodiment also provides the added feature of being able to aspirate the surgical field and to remove tissue and small pieces of bone therefrom.

Figure 7:
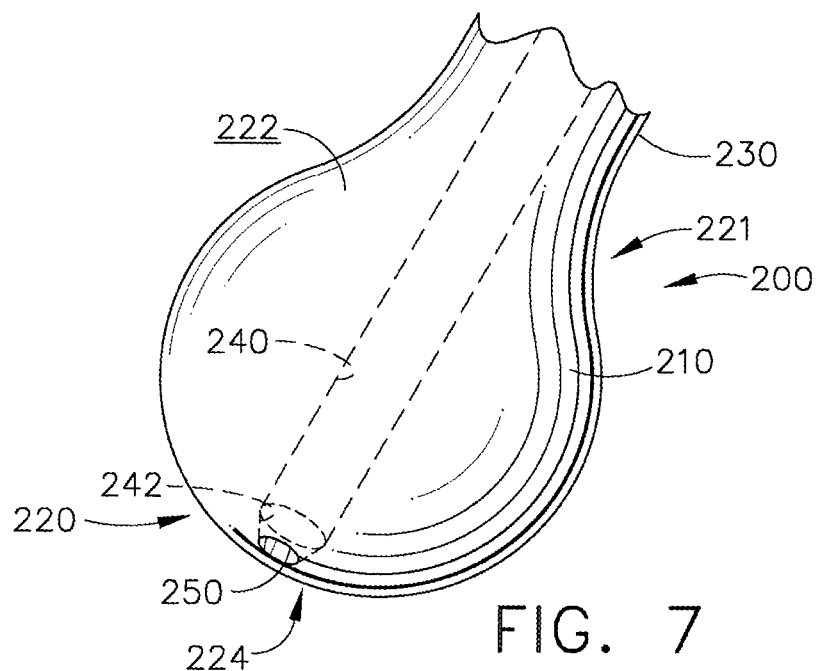
FIG. 7 is a perspective view of a portion of another ultrasonic surgical blade embodiment of the present invention.
Figure 8:
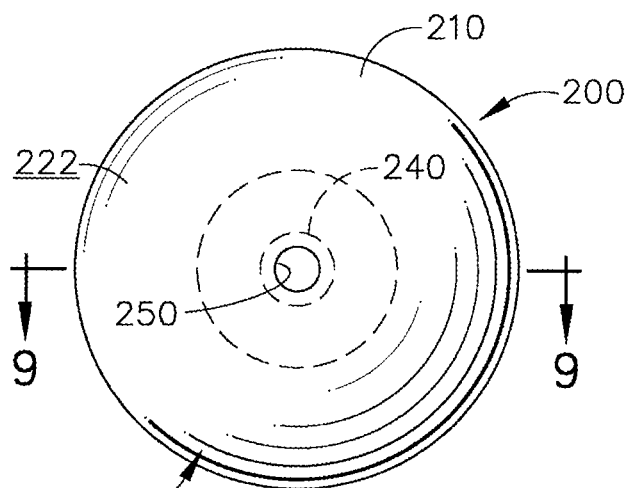
FIG. 8 is an elevational view of a distal end of the ultrasonic surgical blade of FIG. 7.
Figure 9:
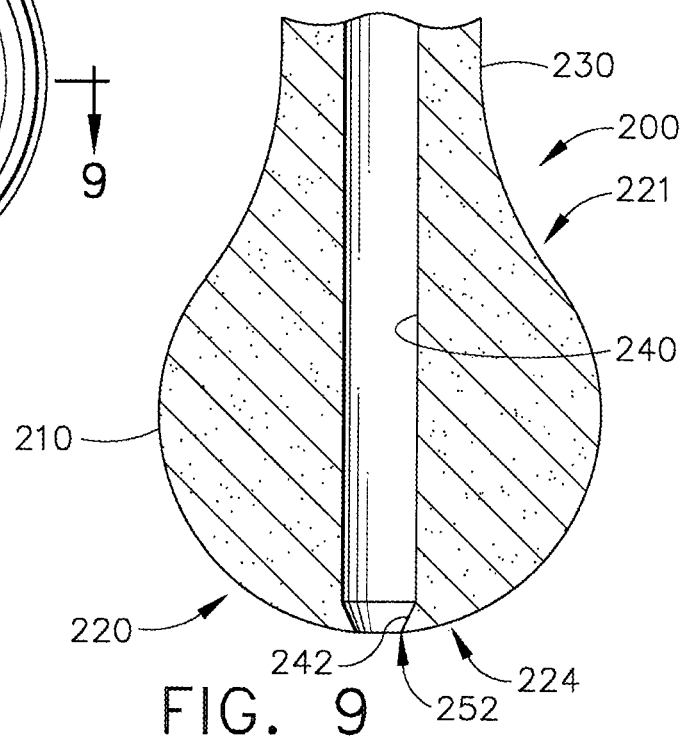
FIG. 9 is a cross-sectional view of the portion of the ultrasonic blade depicted in FIGS. 7 and 8 taken along line 9-9 in FIG. 8.

FIGS. 7-9 illustrate another ultrasonic surgical blade 200 of the present invention. As can be seen in those Figures, the blade 200 has a blade body 210 that has a relative smooth outer surface 222 and may be fabricated from any of the materials described above. The blade body 210 may comprise a substantially spherically-shaped treatment region, generally designated as 220 and a neck or transition portion 230 that protrudes from a proximal portion 221 of the treatment region 220. The neck portion 230 may be attached to a waveguide (not shown) by, for example, a stud, welding, gluing, or other known methods. In alternative embodiments, the neck portion 230 and waveguide may comprise a single unit.

In various embodiments, an aspiration lumen 240 may be provided through the treatment region 220 and neck portion 230 and ultimately communicate with a stand alone suction/irrigation module, tower mounted suction 90 and/or irrigation 92 modules (FIG. 1), or an integrated ultrasonic generator/suction/irrigation module in the operating room, for example. Those of ordinary skill in the art will understand that the suction module may be employed to aspirate tissue and fluids away from the surgical site and the irrigation module may be used to supply irrigation fluids to the surgical site. In the present embodiment, the aspiration lumen 240 has a tapered portion 242 that forms an opening 250 in the distal end 224 of the treatment region 220. The opening 250 is defined by a tissue cutting edge 252 formed in the outer surface 222 of the treatment region 220 that can be used to form and reshape tissue and also assist in the removal of cortical bone. In various embodiments, edge 252 may be relatively sharp to assist in the removal of tissue and/or bone. As the tissue and/or bone material is cut away or dislodged, it can be removed from the surgical field through the aspiration lumen 240. One advantage of the tapered portion is that it initially allows for an acute angle at the ball surface, creating a much sharper edge than a straight bore. In addition, the tapered portion 272 narrows the cutting hole to minimize the size of the particles generated by cutting. This increases the likelihood that the size of the particles is smaller than the central lumen and thus minimizing the likelihood that they will become stuck in the lumen.

In alternative embodiments, the tapered portion 272 may be fabricated from a material that has a property or properties that differ from the property/properties of the material from which the blade body 210 is fabricated. For example, such tapered portion 272 may be pressed into the lumen 240 and/or otherwise attached in position by welding, threads, or other suitable fastener arrangements. In various embodiments, the second material may be selected based on its tensile strength, fatigue strength and/or its ability to maintain an edge or other desirable properties.

FIGS. 10-12 illustrate another ultrasonic surgical blade 300 of the present invention. As can be seen in those Figures, the blade 300 has a blade body 310 that has a relatively smooth outer surface 322 and may be fabricated from any of the materials described above. The blade body 310 may comprise a substantially spherically-shaped treatment region, generally designated as 320. A neck or transition portion 330 protrudes from a proximal portion 321 of the treatment region 320. The neck portion 330 may be attached to a waveguide (not shown) by, for example, a stud, welding, gluing, or other known methods. In alternative embodiments, the neck portion 330 and waveguide may comprise a single unit.

In various embodiments, a first aspiration lumen 340 may be provided in the treatment region 320 and neck portion 330 along a longitudinal axis A-A which ultimately communicates with a stand alone suction/irrigation module, tower mounted suction 90 and/or irrigation 92 modules (FIG. 1), or an integrated ultrasonic generator/suction/irrigation module in the operating room, for example. In the present embodiment, the first aspiration lumen 340 intersects a second aspiration lumen 342 in the treatment region 320 that lies along an axis B-B that intersects axis A-A. In various embodiments, axis B-B may be substantially perpendicular to axis A-A as shown in FIGS. 10 and 12. The second aspiration lumen 342 may form two diametrically opposed openings 344, 346 in the treatment region 320. In the present embodiment, opening 344 is defined by an edge 345 and opening 346 is defined by an edge 347. Edges 345, 347 can be used to form and reshape tissue and also assist in the removal of cortical bone. In various embodiments, one or both edges 345, 347 may be relatively sharp to assist in the removal of tissue and/or bone. As the tissue and/or bone material is cut away or dislodged by edges 345, 347, the material can be removed from the surgical field through the lumens 340 and 342. In alternative embodiments, one or both of openings 344, 346 may be formed with a tapered portion of the arrangements described above.

Figure 13:
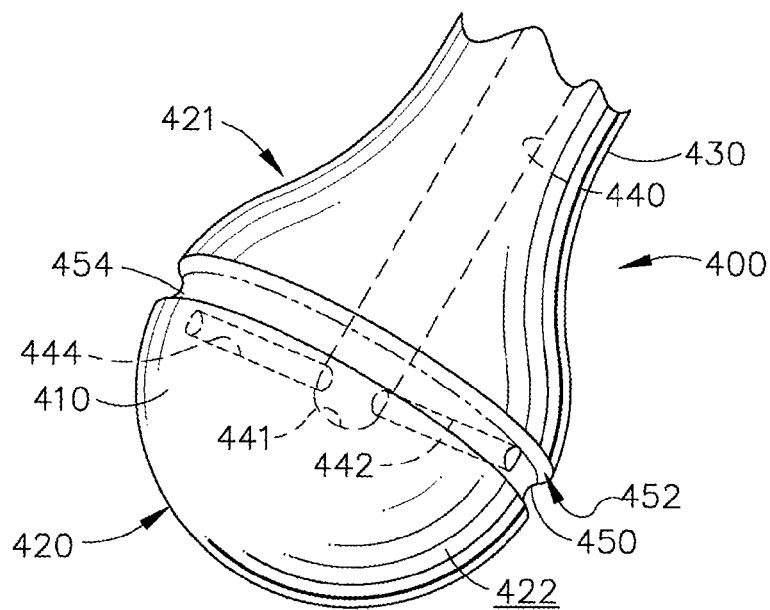
FIG. 13 is a perspective view of a portion of another ultrasonic surgical blade embodiment of the present invention.
Figure 14:
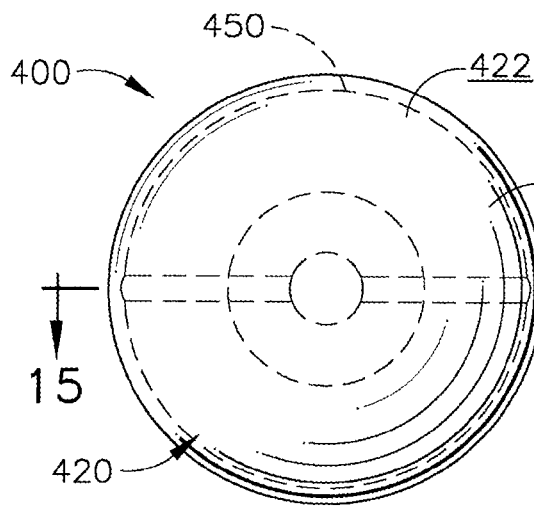
FIG. 14 is an elevational view of a distal end of the ultrasonic surgical blade of FIG. 13.
Figure 15:
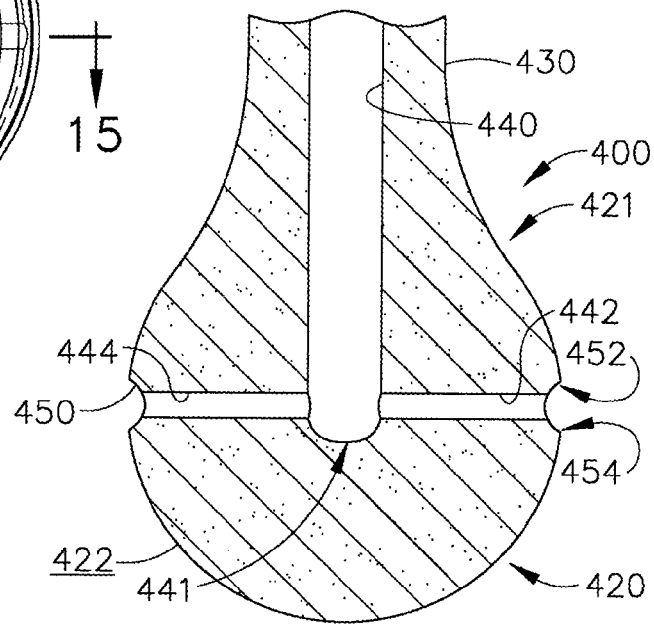
FIG. 15 is a cross-sectional view of the portion of the ultrasonic blade depicted in FIGS. 13 and 14 taken along line 15-15 in FIG. 14.

FIGS. 13-15 illustrate another ultrasonic surgical blade 400 of the present invention. As can be seen in those Figures, the blade 400 has a blade body 410 that has a relatively smooth outer surface 422 and may be fabricated from any of the materials described above. The blade body 410 may comprise a substantially spherically-shaped treatment region, generally designated as 420. In this embodiment, an endless groove 450 is provided around the circumference of the treatment region 420. The groove 450 may have a rounded bottom as shown or it may have a pointed bottom, square bottom, etc. In the illustrated embodiment, the circumferentially extending endless groove 450 forms two parallel edges 452, 454 in the otherwise substantially smooth outer surface 422 for cutting and forming tissue and for providing a bearing surface to remove bone and tissue. A neck or transition portion 430 can protrude from a proximal portion 421 of the treatment region 420. The neck portion 430 may be attached to a waveguide (not shown) by, for example, a stud, welding, gluing, or other known methods. In alternative embodiments, the neck portion 430 and waveguide may comprise a single unit.

Figure 16:
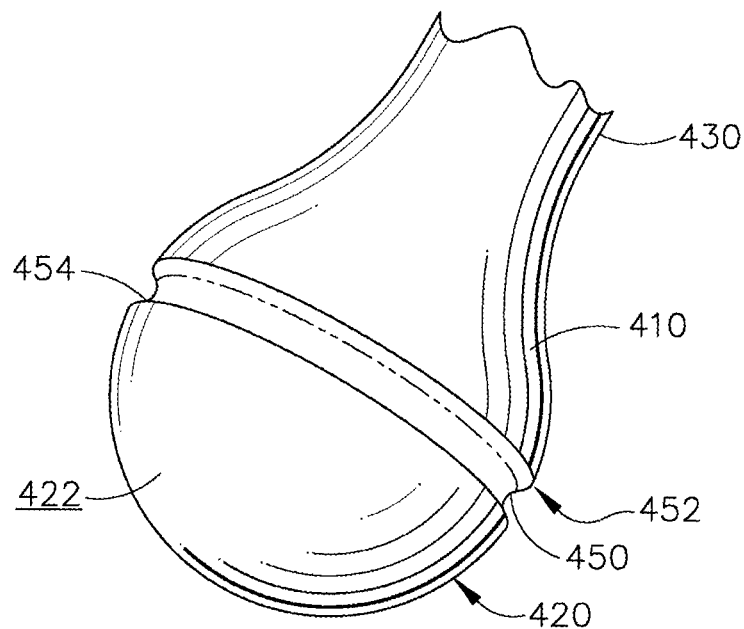
FIG. 16 is a perspective view of a portion of another ultrasonic surgical blade embodiment of the present invention.
Figure 17:
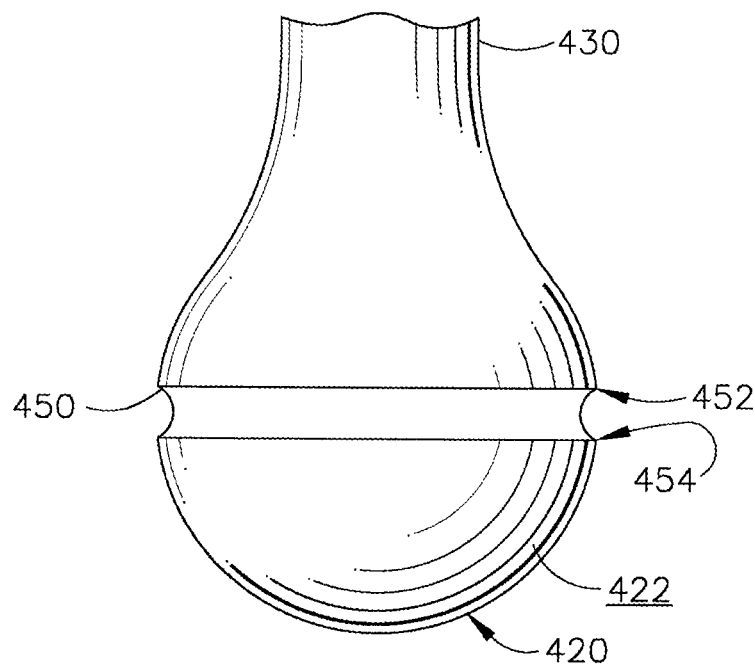
FIG. 17 is a top view of the ultrasonic surgical blade of FIG. 16.

In various embodiments, an aspiration lumen 440 may be provided in the treatment region 420 and neck portion 430 which ultimately communicates with a stand alone suction/irrigation module, tower mounted suction 90 and/or irrigation 92 modules (FIG. 1), or an integrated ultrasonic generator/suction/irrigation module in the operating room, for example. In this embodiment, at least one, but preferably two, cross lumens 442, 444 can extend from the closed end 441 of lumen 440 in diametrically opposed directions and open into the endless groove 450 as shown. As the tissue and/or bone material is cut away or dislodged by edges 452, 454, the material can be removed from the surgical field through the lumens 444, 442, and 440. In the embodiment depicted in FIGS. 13-15, one endless groove 450 is shown. In the illustrated embodiment, the groove extends around the circumference such that it is substantially perpendicular to the neck. In other embodiments, one or more grooves may be formed around body such that they are not perpendicular to the neck portion—e.g., they extend vertically. In alternative embodiments, a plurality of endless grooves may be employed. In still other embodiments, a plurality of discrete grooves may be provided in the relatively smooth outer surface 412. Those discrete grooves may be arranged along substantially parallel axes or they may be axially aligned along a single axis. Those of ordinary skill in the art will also understand that one, two, or more than two cross-lumens may be employed. Such cross lumens may either open into a groove or the outer surface 422 and also open into the aspiration lumen 430. In still other embodiments, one or more cross-lumens may open into a groove and one or more other cross-lumens may open through the surface 422. Those of ordinary skill in the art will understand that, in those embodiments wherein only one cross lumen is employed, such arrangement may result in an imbalance in the blade that may also generate some desirable transverse motions. In still other embodiments wherein only one cross-lumen is employed, such "primary" imbalance caused by only a single cross-lumen may be neutralized by a cavity or similar area (a "secondary" imbalance) provided in another portion of the blade or the cross-lumen could be made small enough to minimize any imbalance created thereby. In other embodiments as shown in FIGS. 16 and 17, no lumens are provided in blade body 410.

FIGS. 18-20 illustrate another ultrasonic surgical blade 500 of the present invention. As can be seen in those Figures, the blade 500 has a blade body 510 that has a relatively smooth outer surface 522 and may be fabricated from any of the materials described above. The blade body 510 may comprise a substantially spherically-shaped treatment region, generally designated as 520. In this embodiment, at least one discreet hole 550 is provided in the treatment region 520. In the embodiment shown in FIGS. 18-20, four holes 550 are shown. In various embodiments, the number and arrangement of holes 550 may vary. Each hole 550 can form an opening 552 in the treatment region 520 that forms a tissue cutting edge 554 in the outer surface 422 that can be used to form and reshape tissue and also assist in the removal of cortical bone. The holes 550 may have a flat bottom 555 as shown or the bottoms may be rounded, pointed, etc. One or more of the holes 550 may have a tapered portion 551 to further facilitate formation of a sharpened edge 554. In the illustrated embodiment, a neck or transition portion 430 can protrude from a proximal portion 521 of the treatment region 520. The neck portion 530 may be attached to a waveguide (not shown) by, for example, a stud, welding, gluing, or other known methods. In alternative embodiments, the neck portion 430 and waveguide may comprise a single unit.

Figure 21:
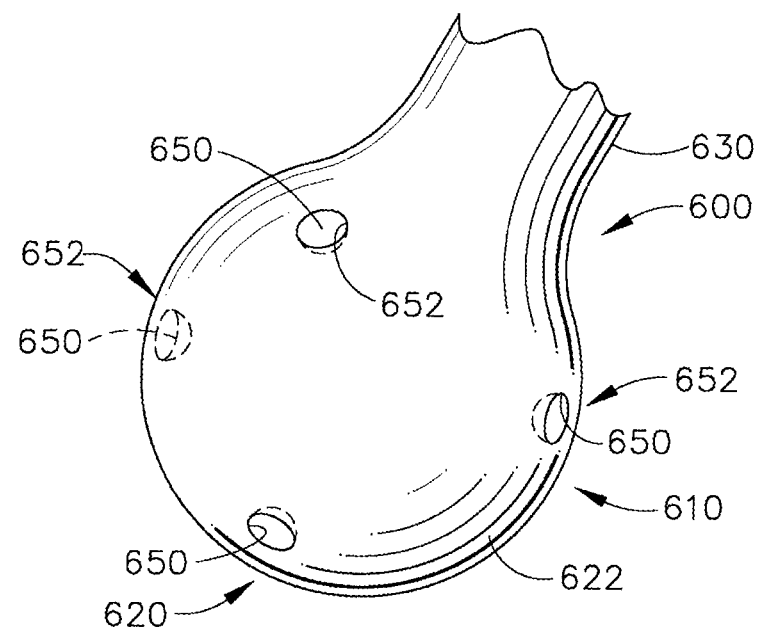
FIG. 21 is a perspective view of a portion of another ultrasonic surgical blade embodiment of the present invention.
Figure 22:
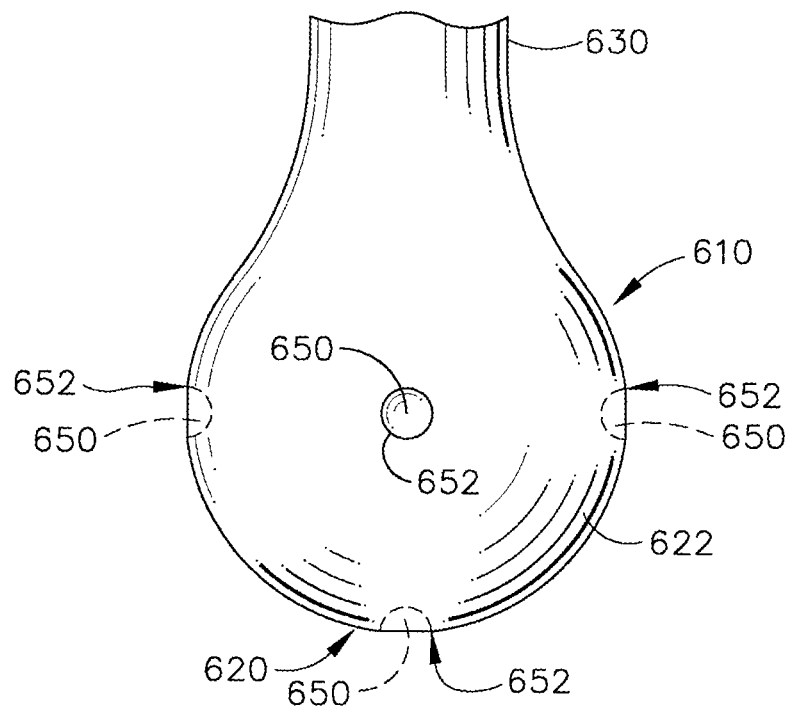
FIG. 22 is a top view of the portion of the ultrasonic blade of FIG. 21.

FIGS. 21 and 22 illustrate another ultrasonic surgical blade 600 of the present invention. As can be seen in those Figures, the blade 600 has a blade body 610 that has a relatively smooth outer surface 622 and may be fabricated from any of the materials described above. The blade body 610 may comprise a substantially spherically-shaped treatment region, generally designated as 620. In this embodiment, at least one dimple 650 is provided in the treatment region 620. In the embodiment shown in FIGS. 21 and 22, four dimples 650 are shown. In various embodiments, the number and arrangement of dimples 650 may vary. Each dimple 650 can form a tissue cutting edge 652 in the exterior surface 622 that can be used to form and reshape tissue and also assist in the removal of cortical bone. In the illustrated embodiment, a neck or transition portion 630 protrudes from a proximal portion of the treatment region 620. The neck portion 630 may be attached to a waveguide (not shown) by, for example, a stud, welding, gluing, or other known methods. In alternative embodiments, the neck portion 630 and waveguide may comprise a single unit.

Figure 23:
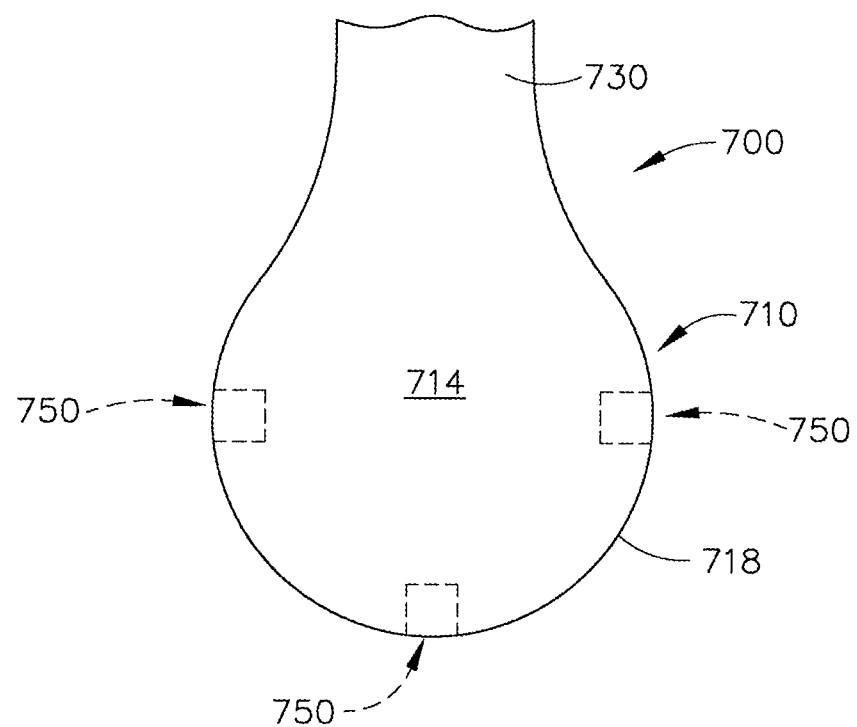
FIG. 23 is a top view of a portion of another ultrasonic surgical blade embodiment of the present invention.
Figure 24:
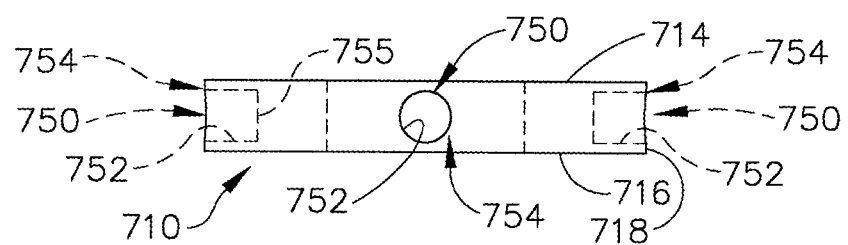
FIG. 24 is an elevational view of a distal end of the ultrasonic surgical blade of FIG. 23.

FIGS. 23 and 24 illustrate another ultrasonic surgical blade 700 of the present invention. As can be seen in those Figures, the blade 700 has a body 710 that has a rounded distal end 712 and two relatively planar surfaces 714 and 716 that are separated by a side surface 718. Blade 700 may be fabricated from any of the materials described above. The body 710 may comprise a treatment region, generally designated as 720. In this embodiment, at least one hole 750 is provided in the side 718 of the body 710. In the embodiment shown in FIGS. 23 and 24, three holes 750 are shown. In various embodiments, the number and arrangement of holes 750 may vary. Each hole 750 can form an opening 752 in the body portion 710 that forms an edge 754 that can be used to form and reshape tissue and also assist in the removal of cortical bone. In one embodiment, the holes 750 may be in fluid communication with a central lumen for irrigation and aspiration of tissue during cutting. The holes 750 may have a flat bottom 755 as shown or the bottoms may be rounded, pointed, etc. In the illustrated embodiment, a neck or transition portion 730 protrudes from a proximal portion of the treatment region 720. The neck portion 730 may be attached to a waveguide (not shown) by, for example, a stud, welding, gluing, or other known methods. In alternative embodiments, the neck portion 730 and waveguide may comprise a single unit.

The various embodiments of the present invention described herein, as well as their equivalent structures, represent a vast improvement over prior ultrasonic surgical blade configurations. For example, several of the embodiments disclosed herein include a treatment region that is substantially spherical in shape and has a relatively smooth outer surface which can be advantageously employed to coagulate and reshape tissue. In addition, several of the embodiments disclosed herein have one or more tissue cutting edges formed in the treatment region thereof which can be used to cut and shave tissue and may also serve as bearing surfaces that can be used to engage and remove portions of cortical bone when an impact force is applied to the instrument by conventional means (mallet, etc.). These edges may be advantageously sharpened utilizing files or other conventional sharpening tools or, if desired, the edges may be relatively dull. A variety of different structures have been disclosed for forming the edges in the otherwise smooth exterior surface of the body portion. In general, the edges may be formed by indentations in the outer surface of the body portion. As used in this context, the term "indentation" may comprise, for example, a discrete hole (i.e., a hole that does not pass completely through any portion of the body), a lumen or passageway that forms an opening in the outer surface and passes through the body member, a groove or series of grooves formed in the outer surface of the body portion, dimples and/or any combination of these indentations. The number and orientations of such "indentations" may vary without departing from the spirit and scope of the present invention and provided that a desired amount of relatively smooth surface is maintained for coagulation and tissue shaping purposes.

Thus, as can be appreciated form the foregoing, various embodiments of the present invention provide a faster and more precise method for removing cortical bone. Such arrangements may also require less force to remove bone than prior bone removal methods. In addition, the unique and novel features of various embodiments of the present invention also facilitate spot coagulation of tissue with out the need to use radio frequency-based means which can create deep thermal injury to the tissue.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The blades and devices disclosed herein can be designed to be disposed of after a single use, or they can be designed to be used multiple times. In either case, however, the device may be reconditioned for reuse after at least one use. Reconditioning can include a combination of the steps of disassembly of the device, followed by cleaning or replacement of particular pieces, and subsequent reassembly. In particular, the device may be disassembled, and any number of particular pieces or parts of the device can be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam, autoclaving, soaking in sterilization liquid, or other known processes.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. An ultrasonic surgical blade, comprising:
   an ultrasonic transmission member;
   a substantially spherically-shaped blade body protruding from said ultrasonic transmission member and having a treatment region;
   a first lumen extending at least partially through said ultrasonic transmission member and at least a portion of said blade body;
   at least two dimples formed in said treatment region of said blade body wherein each dimple forms a tissue cutting edge with an outer surface of said blade body; and
   at least one second lumen extending at least partially through another portion of said blade body and intersecting said first lumen for fluid communication therewith, wherein said at least one second lumen is in fluid communication with said at least two dimples.

2. The ultrasonic surgical blade of claim 1, wherein said at least one second lumen extends along an axis that is substantially perpendicular to a longitudinal axis.

3. The ultrasonic surgical blade of claim 2, wherein said ultrasonic transmission member is configured to transmit at least one of a longitudinal motion, transverse motion and torsional motion from a corresponding source of said longitudinal motion, transverse motion, and torsional motion communicating therewith to said blade body.

4. The ultrasonic surgical blade of claim 3, wherein said ultrasonic transmission member is configured to transmit a combination of said longitudinal motion, transverse motion, and torsional motion to said blade body.

5. The ultrasonic surgical blade of claim 1 further comprising an aspiration member communicating with said first lumen.

6. The ultrasonic surgical blade of claim 1, wherein said first lumen is in fluid communication with at least one of an aspiration module and an irrigation module.

7. An ultrasonic surgical instrument, comprising:
   a fluid motivation module;
   a transducer; and
   an ultrasonic surgical blade, comprising:
      an ultrasonic transmission member;
      a blade body protruding from said ultrasonic transmission member, said blade body including a treatment region, wherein said blade body comprises a substantially spherically-shaped distal portion;
      a first lumen extending at least partially through said ultrasonic transmission member and at least a portion of said blade body;
      an inlet distal to said transducer, said inlet configured to couple said first lumen to said fluid motivation module;
      a plurality of dimples formed in said treatment region of said blade body wherein each dimple forms a tissue cutting edge with an outer surface of said blade body; and
      at least one second lumen extending at least partially through another portion of said blade body and intersecting said first lumen for fluid communication therewith, wherein said at least one second lumen is in fluid communication with said plurality of dimples.

8. The ultrasonic surgical instrument of claim 7, wherein said at least one second lumen extends along an axis that is substantially perpendicular to a longitudinal axis.

9. The ultrasonic surgical instrument of claim 7, wherein said ultrasonic transmission member is configured to transmit at least one of a longitudinal motion, transverse motion and torsional motion from a corresponding source of said longitudinal motion, transverse motion, and torsional motion communicating therewith to said blade body.

10. The ultrasonic surgical instrument of claim 9, wherein said ultrasonic transmission member is configured to transmit a combination of said longitudinal motion, transverse motion, and torsional motion to said blade body.

11. The ultrasonic surgical instrument of claim 7 further comprising an aspiration member communicating with said first lumen.

12. The ultrasonic surgical instrument of claim 7, wherein said first lumen is in fluid communication with at least one of an aspiration module and an irrigation module.

* * * * *